US005569275A

United States Patent [19]
Kotula et al.

[11] Patent Number: 5,569,275
[45] Date of Patent: Oct. 29, 1996

[54] MECHANICAL THROMBUS MACERATION DEVICE

[75] Inventors: Frank Kotula, Maple Grove; Timothy Claude, Coon Rapids, both of Minn.

[73] Assignee: Microvena Corporation, White Bear Lake, Minn.

[21] Appl. No.: 193,490

[22] Filed: Feb. 8, 1994

Related U.S. Application Data

[63] Continuation-in-part of Ser. No. 713,394, Jun. 11, 1991, Pat. No. 5,284,486.

[51] Int. Cl.⁶ ................................................. A61B 17/32
[52] U.S. Cl. ............................................. 606/159; 606/170
[58] Field of Search .................................. 606/159, 170, 606/171, 180; 604/22

[56] References Cited

U.S. PATENT DOCUMENTS

| | | |
|---|---|---|
| 3,131,469 | 5/1964 | Glaze . |
| 3,614,953 | 10/1971 | Moss . |
| 3,708,241 | 1/1973 | Theis, Jr. et al. . |
| 4,060,336 | 11/1977 | Theis et al. . |
| 4,589,412 | 5/1986 | Kensey ..................................... 606/159 |
| 4,664,112 | 5/1987 | Kensey et al. . |
| 4,681,106 | 7/1987 | Kensey et al. ........................... 606/180 |
| 4,686,982 | 8/1987 | Nash . |
| 4,784,636 | 11/1988 | Rydell ....................................... 604/22 |
| 4,857,045 | 8/1989 | Rydell ....................................... 606/159 |
| 4,917,085 | 4/1990 | Smith . |
| 4,926,860 | 5/1990 | Stice et al. . |
| 4,944,722 | 7/1990 | Carriker et al. . |
| 4,986,807 | 1/1991 | Farr . |
| 5,007,917 | 4/1991 | Evans . |
| 5,067,489 | 11/1991 | Lind . |
| 5,084,052 | 1/1992 | Jacobs . |
| 5,250,060 | 10/1993 | Carbo et al. . |
| 5,284,486 | 2/1994 | Kotula et al. ........................... 606/159 |

FOREIGN PATENT DOCUMENTS

| | | |
|---|---|---|
| 0147192 | 7/1985 | European Pat. Off. . |
| 0289319 | 11/1988 | European Pat. Off. . |
| 0310685 | 4/1989 | European Pat. Off. . |
| 1350393 | 6/1986 | U.S.S.R. . |
| 8705795 | 10/1987 | WIPO . |
| 9013329 | 11/1990 | WIPO . |
| 9222253 | 12/1992 | WIPO . |

OTHER PUBLICATIONS

Schmitz-Rode, et al., "Percutaneous Mechanical Thrombolysis, A Comparative Study of Various Rotational Catheter Systems", Investigative Radiology, Jun. 1991, vol. 26, pp. 557–563.

Yedlicka, Jr., et al., "Thrombectomy with the Transluminal Endarterectomy Catheter (TEC) System:Experimental Study and Case Report", J. Vascular and Interventional Rad. Aug. 1991, pp. 343–347.

(List continued on next page.)

*Primary Examiner*—Stephen C. Pellegrino
*Assistant Examiner*—William Lewis
*Attorney, Agent, or Firm*—Fredrikson & Byron, PA

[57] ABSTRACT

In one embodiment, the present invention provides a mechanical thrombus maceration device which includes a flexible shaft adapted to be guided along a vascular path and rotated within a vascular channel; a rotor affixed to the shaft adjacent the distal end thereof for rotation therewith; drive means for rotating the shaft; and a rotor housing within which the rotor rotates. The rotor housing of this embodiment comprises a generally cylindrical wall substantially surrounding the rotor and having at least one port formed therein, the port or ports being positioned about the housing such that when a fluid (e.g. blood) is ejected through the ports within a vascular channel, the housing will tend to deflect toward one side of the vascular channel to permit the device to be steered during deployment. In another embodiment of the invention, the device includes an elongate, flexible shaft adapted to be guided along a vascular path and which is rotatable within a vascular channel; a plurality of rotors spaced from one another along the shaft and attached to the shaft for rotation therewith; drive means for rotating the shaft; and a rotor housing enclosing at least one of the rotors.

18 Claims, 18 Drawing Sheets

OTHER PUBLICATIONS

Hawkins Jr., et al., "Mechanical Spiral Embolectomy Catheter", Seminars in Interventional Radiology, vol. 2, No. 4, Dec. 1985, pp. 414–418.

Ritchie, et al., "Thrombolysis: A New Rotational Thrombectomy Catheter and Evaluation by Angioscopy", International Symposium on Interventional Cardiology, Sep. 21–23, 1986, pp. 323–324.

Hansen, et al., "In Vivo Mechanical Thrombolysis in Subacute Canine Arterial Occlusion", Abstracts of the 58th Scientific Sessions, III–469, p. 300.

Ritchie, et al., "Rotational Guiddewire Thrombectomy; In Vivo Canine thrombus Disruption and Removal", JACC vol. 5, No. 2, Feb. 1985:440, p. 314.

Guenther, et al., "Aspiration Catheter for Percutaneous Thrombectomy; Clinical Results", vol. 175, Radiology No. 1: 271–273 Apr. 1991.

Bildsoe, et al., "Mechanical Clot Dissolution: New Concept", vol. 171 Radiology No. 1: 231–233; Apr. 1989.

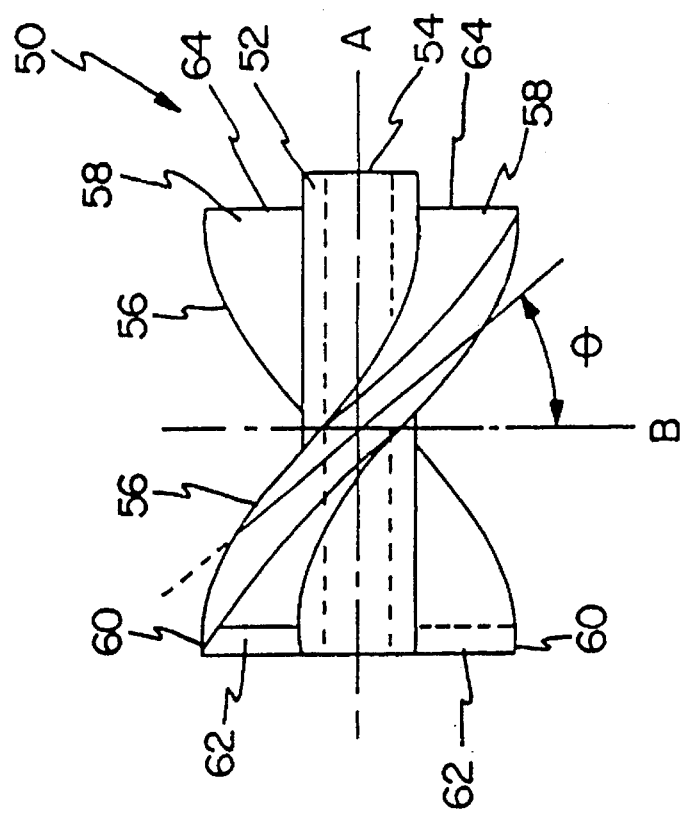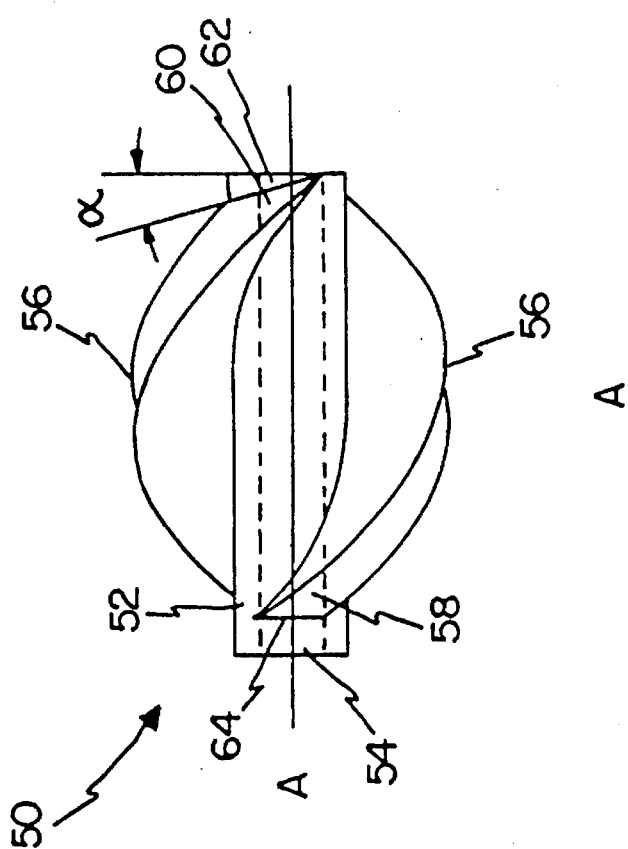
Fig. 4

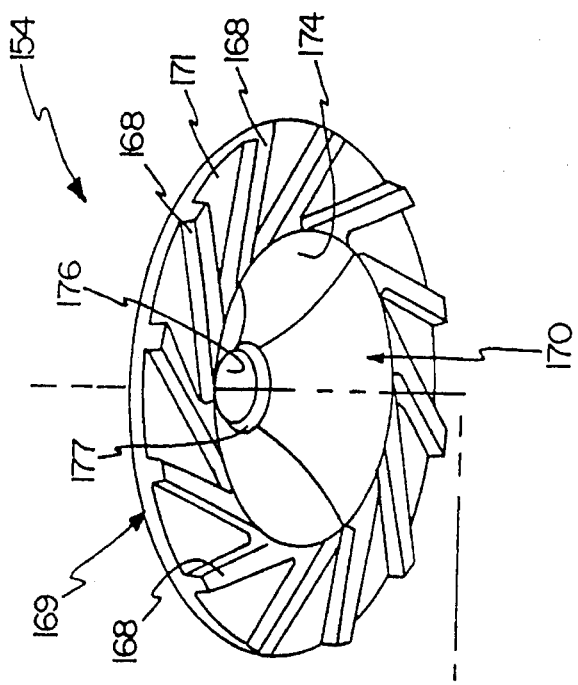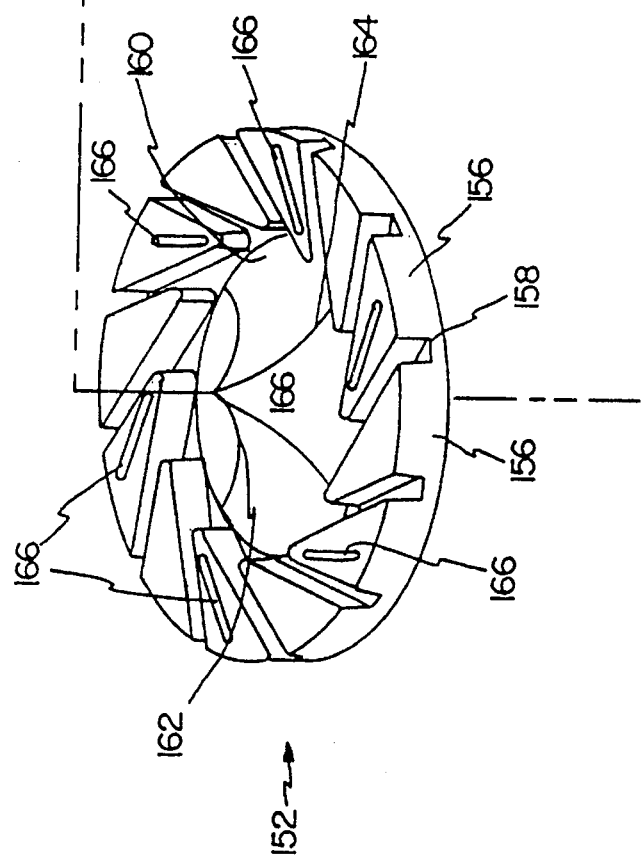
Fig. 9

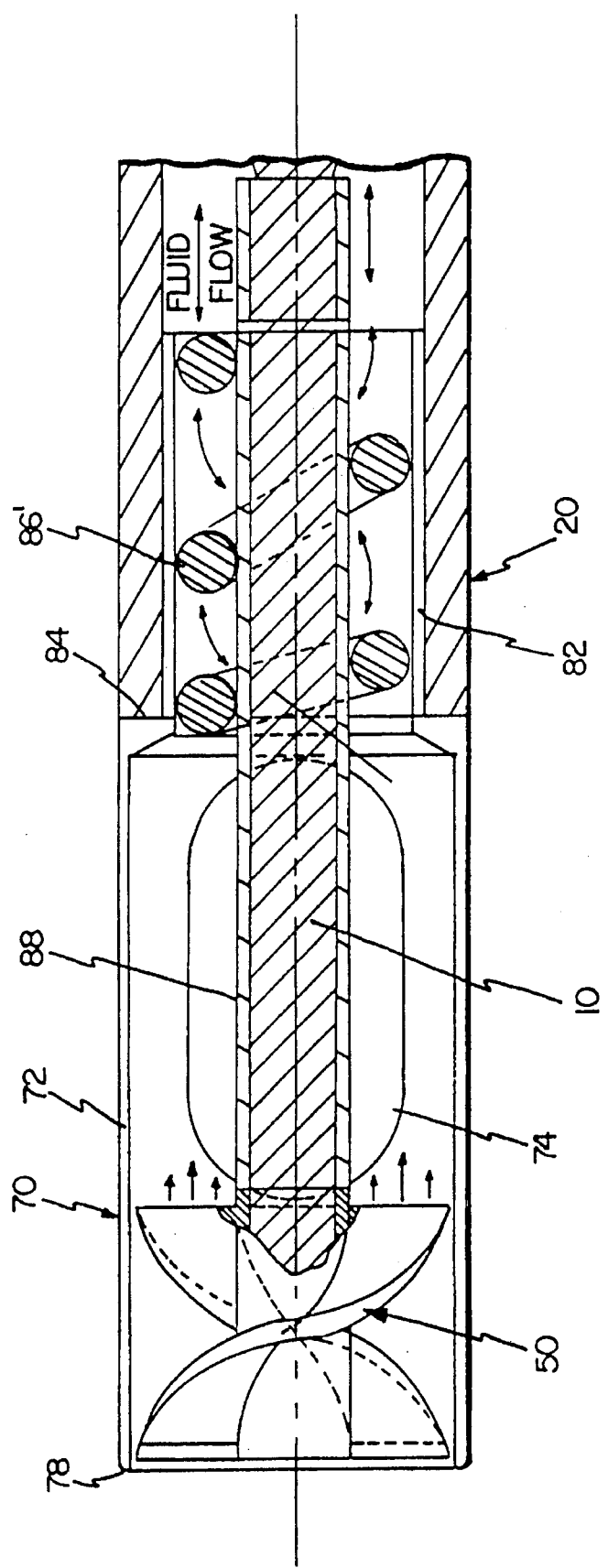

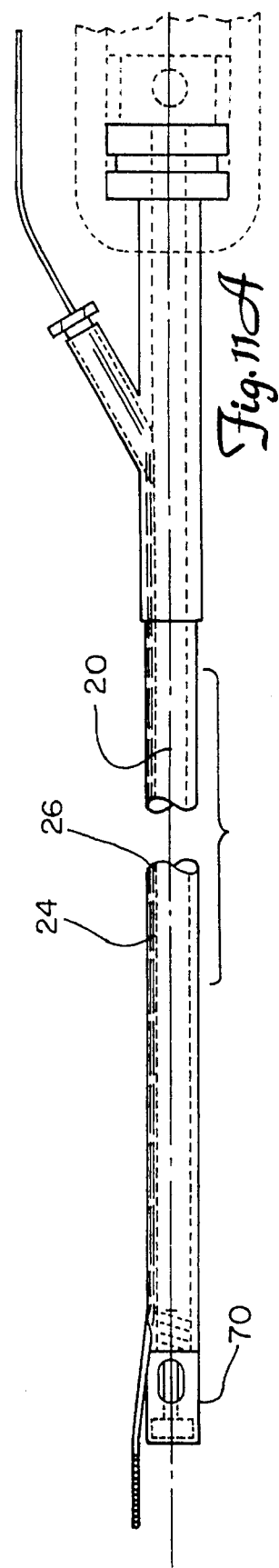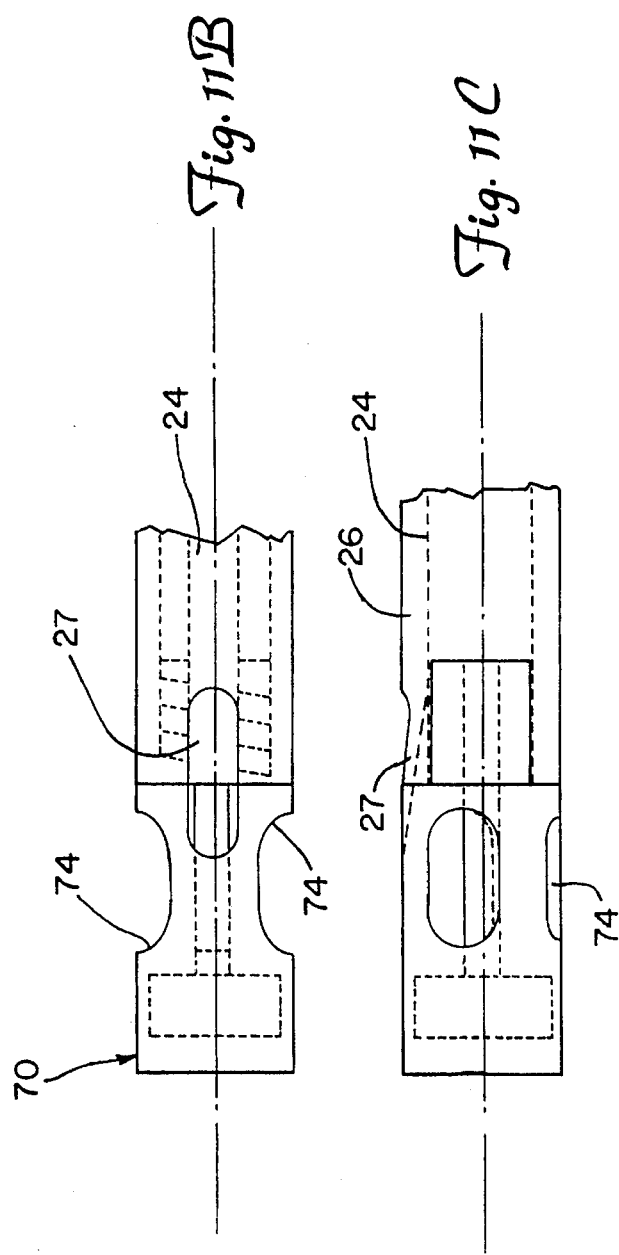

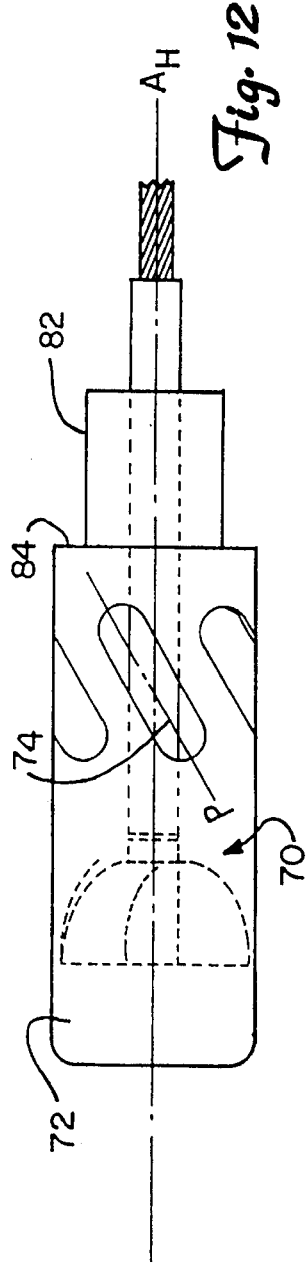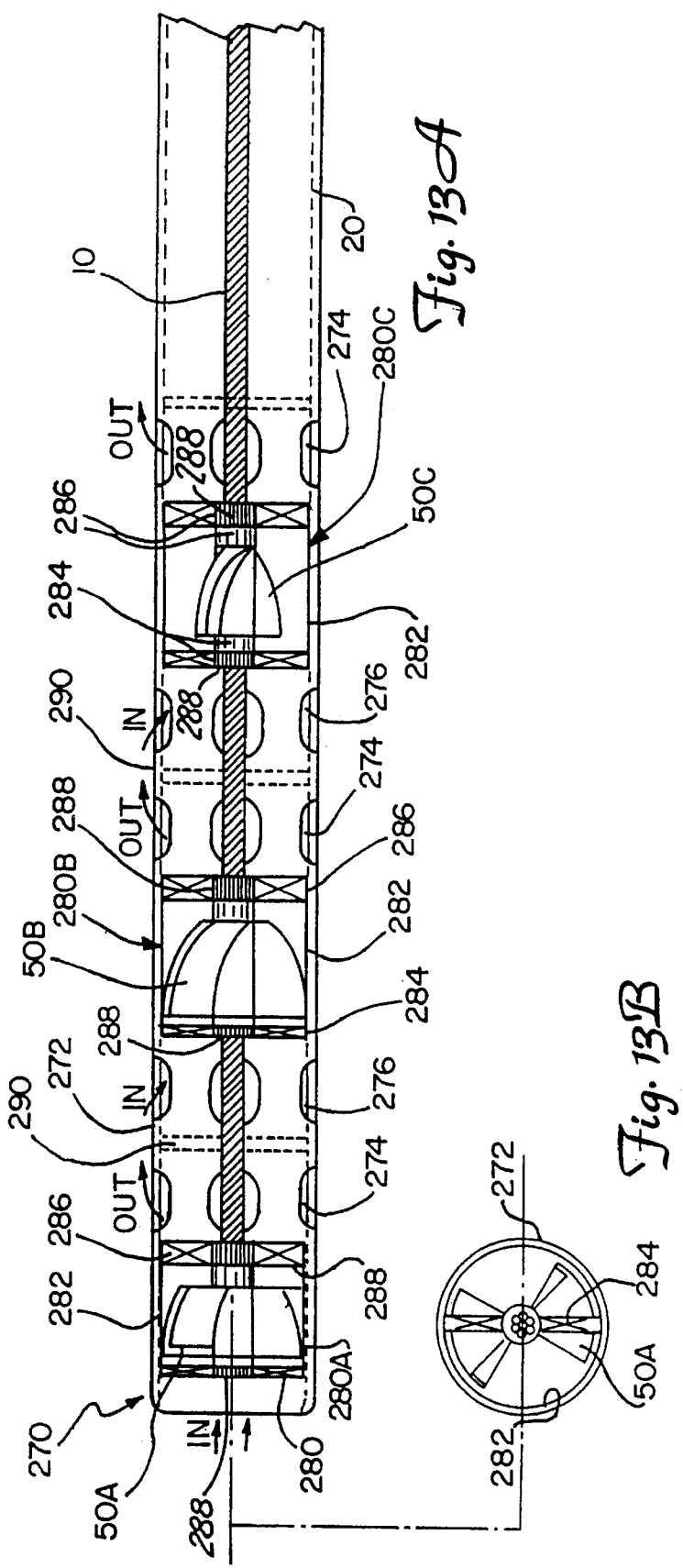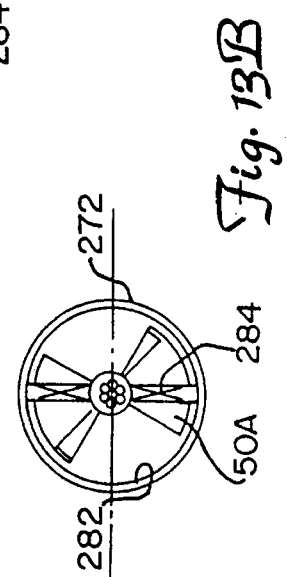

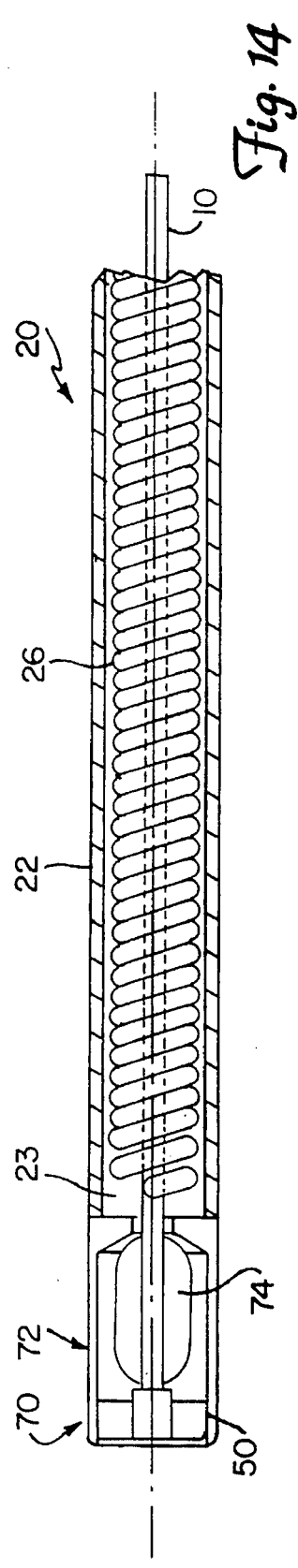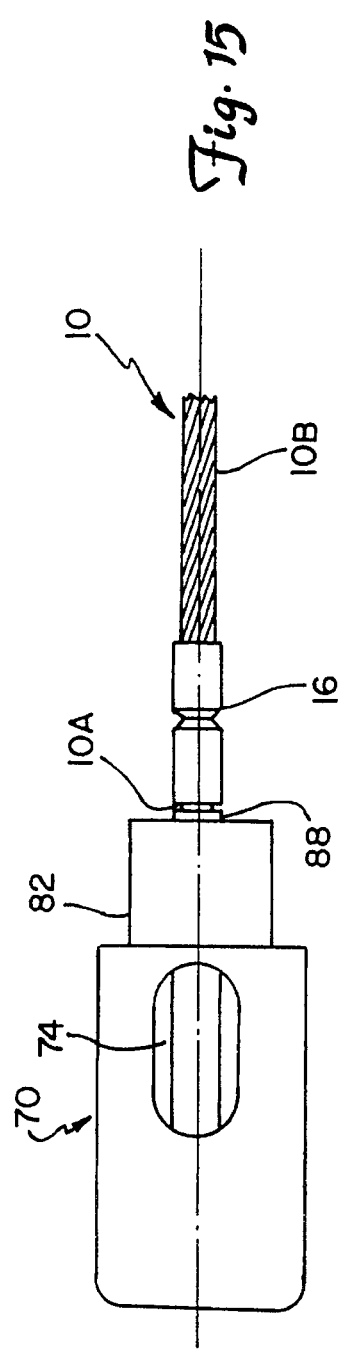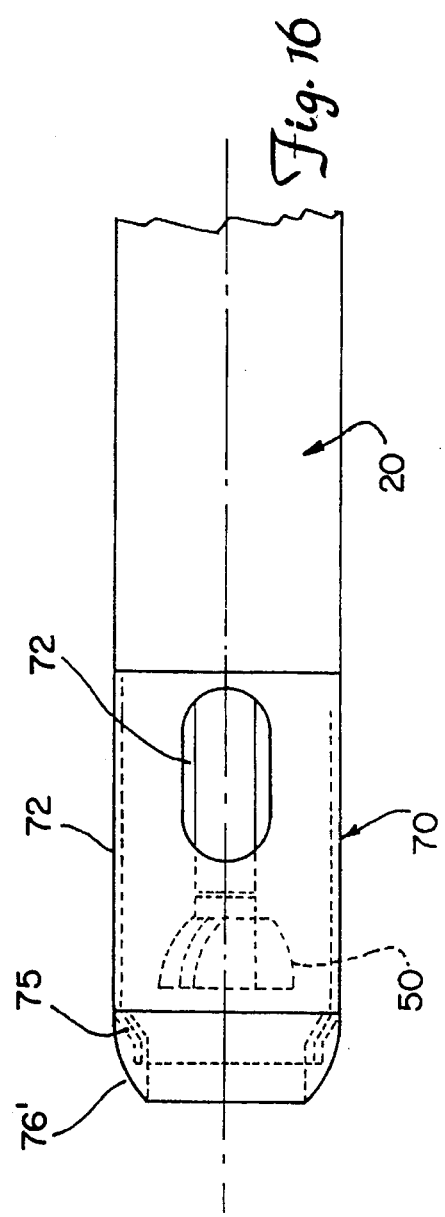

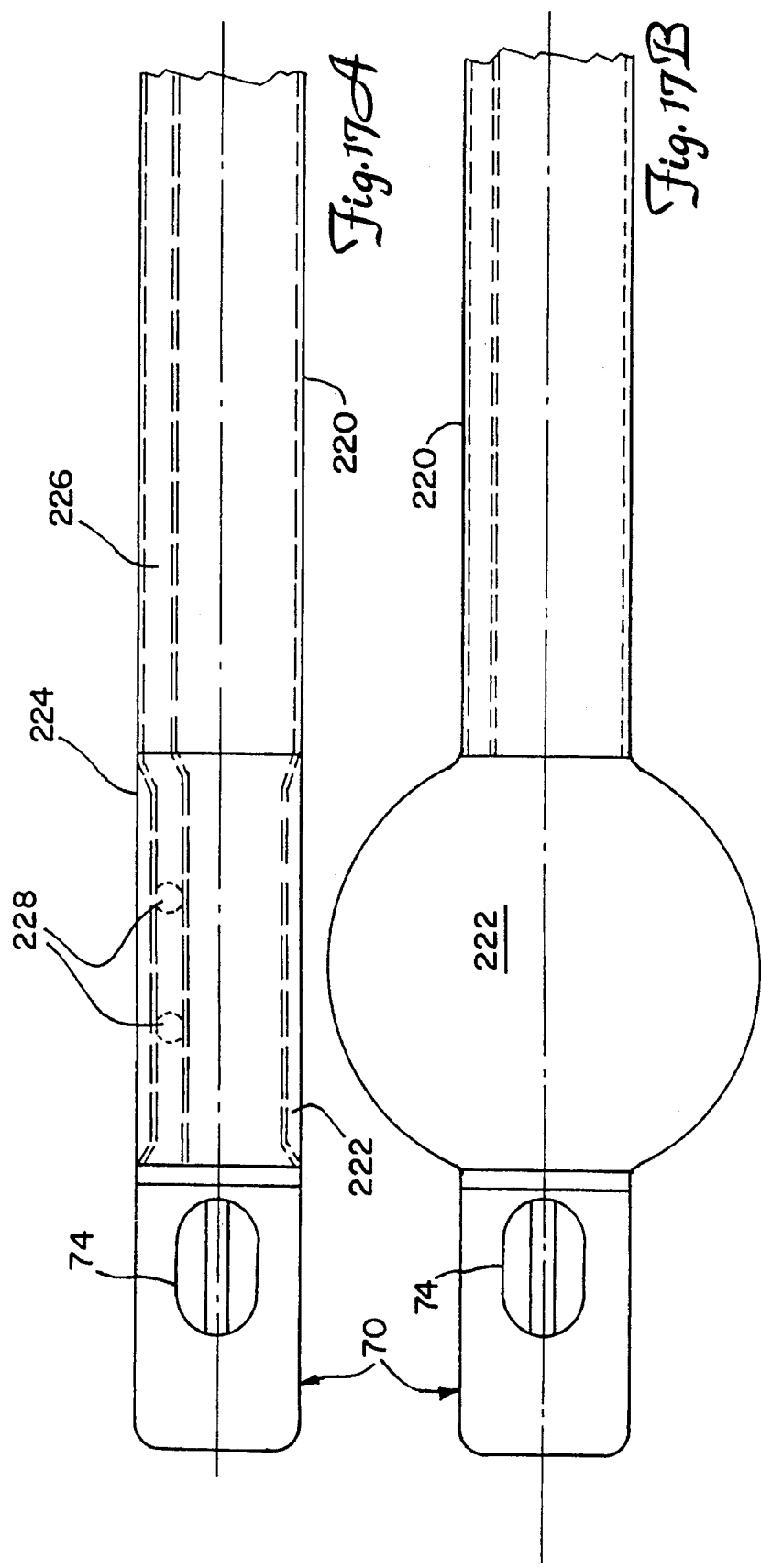

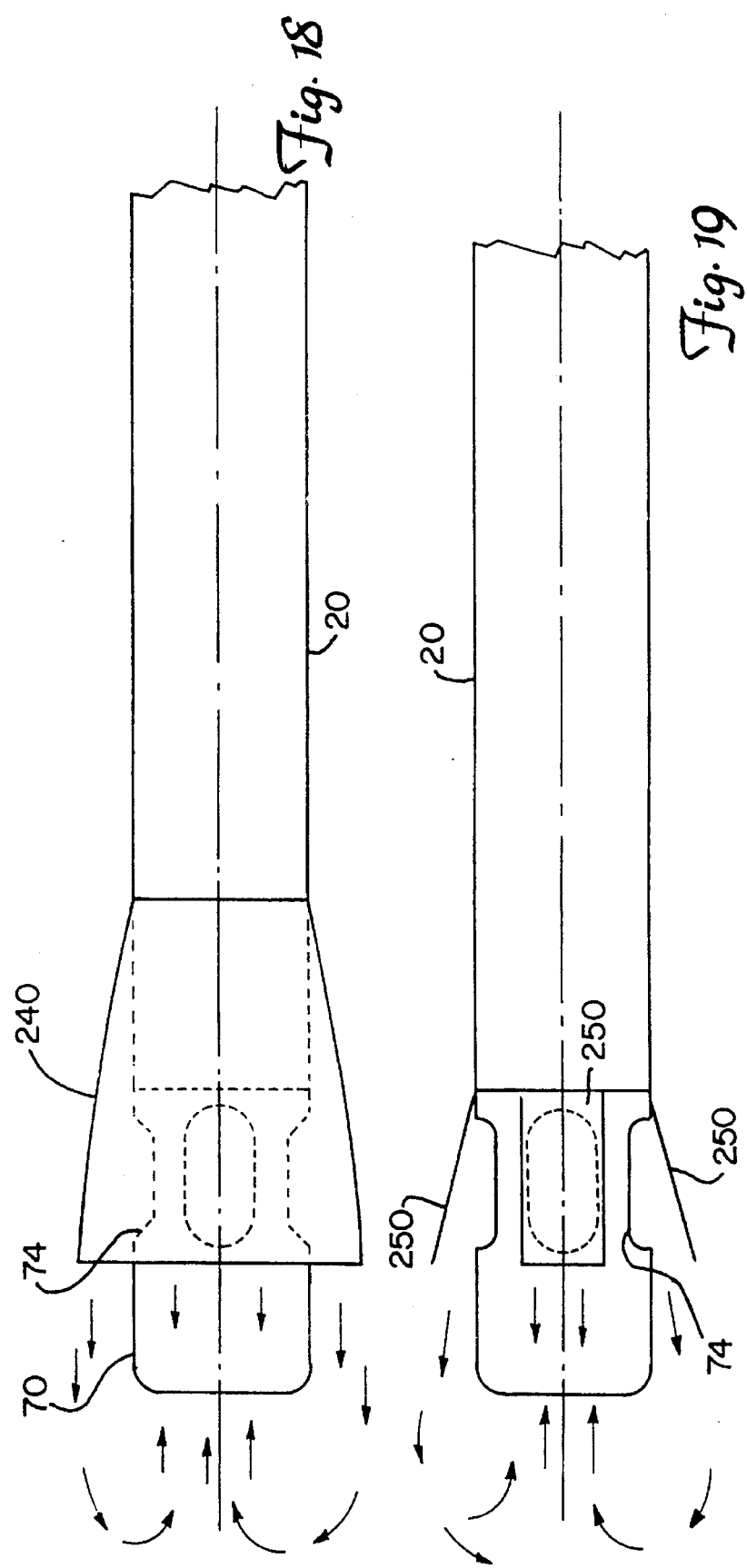

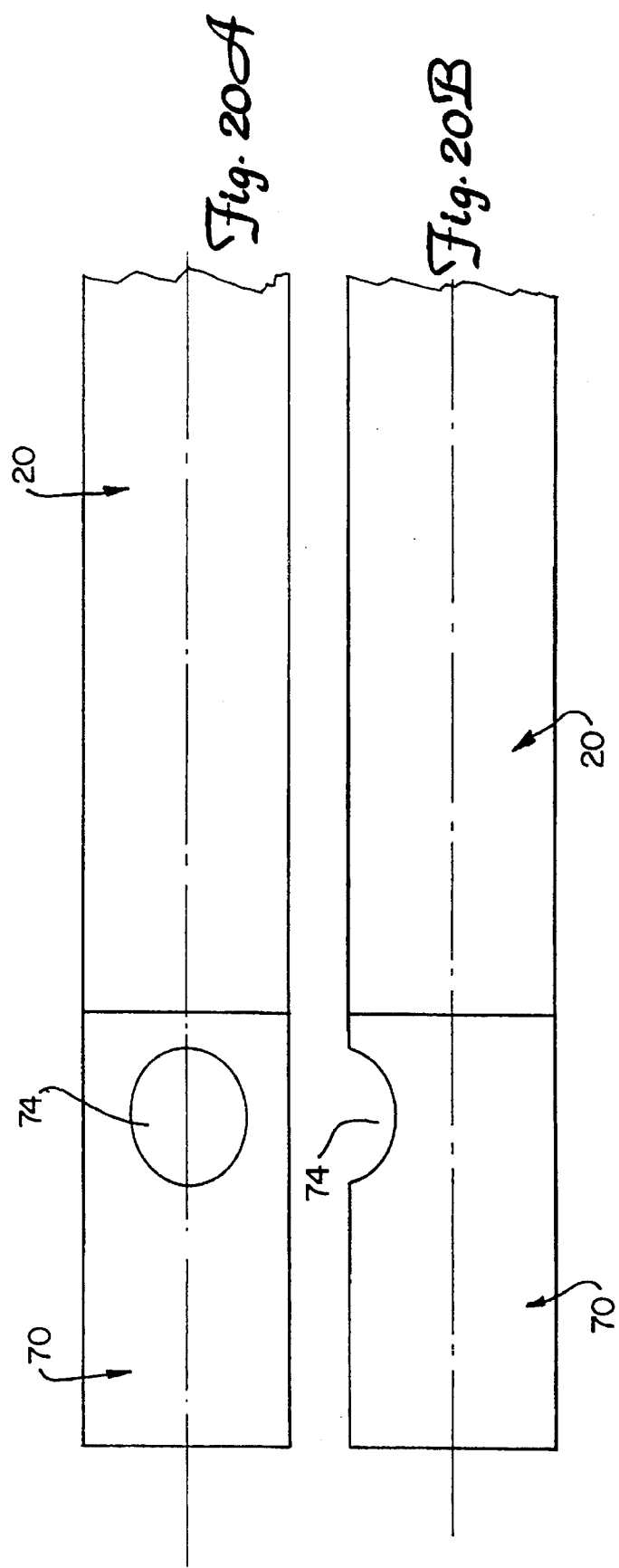

MECHANICAL THROMBUS MACERATION DEVICE

This application is a continuation-in-part of application Ser. No. 07/713,394 filed Jun. 11, 1991, now U.S. Pat. No. 5,284,486.

FIELD OF THE INVENTION

The present invention provides a medical device for use in vascular procedures. The device is particularly useful in the mechanical maceration of a thrombus or the like.

BACKGROUND OF THE INVENTION

It is well known that the presence of foreign solid matter within an individual's vascular system can have serious adverse effects on an individual's health, either directly or indirectly. Such solid matter most commonly takes either the form of a thrombus, i.e., gelatinous, free-floating matter within a vascular channel but not adhered to the channel itself, or atheroma, which is most commonly a buildup of plaque or the like on the wall of a vessel. A wide variety of techniques are known for removing or breaking down such matter within the vascular system. Some techniques, known as thrombolytic therapy, utilize pharmaceutical compounds, e.g., urokinase or streptokinase, to help dissolve such foreign matter.

Other techniques take a mechanical approach and attempt to dislodge the solid matter from the walls of the vascular system, if necessary, and then remove the solid matter from the vascular system by means of suction or the like. In dislodging plaque from vascular walls, an elongate wire with one or more scraping blades adjacent the distal end is rotated within the vascular channel. By moving the rotating blades axially into contact with the plaque, the blades will tend to dislodge it, permitting the dislodged particulate matter to be withdrawn from the vascular system by means of suction through a catheter or the like. A similar technique may also be used to break a relatively large thrombus into a number of smaller pieces which may then be extracted by aspiration.

This prior art technique does have a number of significant disadvantages, though. First, the rotating blades, which commonly rotate at between about 2,000 and about 35,000 rpm, are exposed, therefore posing a significant risk of puncturing the wall of an artery or a vein. It is estimated that this occurs in up to one-third of the procedures carried out with such a rotating blade, posing serious health risks each time such a device is used.

Another disadvantage of this procedure is that it is unable to finely grind the particulate matter; it simply tends to dislodge relatively large pieces of the built up plaque or break a large thrombus into a small number of individual pieces which remain fairly large themselves. Because this free-floating solid matter would tend to form additional thrombi if permitted to remain in the vascular system, they must be removed. As noted above, this is most commonly done by attempting to draw the thrombi out of the body through a catheter under suction. In so withdrawing the thrombi, one must necessarily withdraw a significant amount of blood as well. The volume of blood withdrawn from the patient must obviously be replaced, so additional blood supplies must be available for transfusion into the patient undergoing this procedure.

Accordingly, it would be desirable to provide a means of reliably breaking down a thrombus or the like sufficiently to permit the resulting small particles to be left within the vascular system without any significant disadvantage. Additionally, it would be useful to provide such a medical device which would be centered within a vascular channel and spaced away from the vascular walls to minimize trauma to the lumen of the vessel and the risk of puncturing the vessel wall.

SUMMARY OF THE INVENTION

The present invention provides a safe, reliable means of breaking down a thrombus with rotating blades into particles which are fine enough to be left in the vascular system without any significant risk of forming additional thrombi. The thrombectomy device also includes means to ensure that the rotating blades of the device do not directly contact the walls of the vessel, but rather remain substantially centered within the vessel.

A medical device according to the present invention generally includes an elongate, flexible shaft which may be guided along a vascular path. A rotor, or "impeller," having blades is affixed to the shaft adjacent its distal end. Drive means are provided for rapidly rotating the shaft and the rotor attached to the shaft. The rotor is retained within a rotor housing and rotates therein. The rotor housing comprises a generally cylindrical wall substantially surrounding the rotor and having at least three ports spaced equiangularly about the circumference of the housing. As the rotor is rotated, it will tend to draw fluid, i.e., blood, into the housing in a proximal direction and expel the fluid out through the ports. This fluid then tends to be drawn back into the distal end of the housing and through the rotor again, setting up a recirculating vortex which repeatedly passes the fluid across the blades.

When the fluid is ejected through the ports in the housing within a vascular channel, the fluid will tend to act against the wall of the channel. This in turn tends to maintain the housing in a position spaced away from the surrounding vascular wall. By spacing the ports equiangularly about the circumference of the housing, the force exerted by the ejected fluid will tend to maintain the housing and the rotor carried therein in a position substantially centered within the vascular channel.

BRIEF DESCRIPTION OF THE DRAWINGS

FIG. 4 is a side view and a rotated side view of a preferred embodiment of a rotor of the invention;

FIG. 9 is an exploded perspective view of a turbine for use in the drive means of FIG. 7;

FIG. 10 is a side view in partial cross section of a distal portion of an alternative embodiment of the invention;

FIG. 11A illustrates an alternative embodiment of the invention of FIG. 6, utilizing an alternative guidewire tracking channel;

FIG. 11B is a top isolation view of a distal portion of the invention of FIG. 11A;

FIG. 11C is a side isolation view of a distal portion of the invention of FIG. 11A;

FIG. 12 illustrates an alternative embodiment of a rotor housing of the invention;

FIGS. 13A and 13B are a side elevational view and an end view, respectively, of another embodiment of the invention, which employs a multi-stage rotor design;

FIG. 14 is a side view in partial cross section of a distal portion of yet another embodiment of the invention;

FIG. 15 is a schematic view of a shaft in accordance with one embodiment of the invention;

FIG. 16 is a side view of a distal portion of another embodiment of a housing of the invention;

FIG. 17A is a side view of a further embodiment of the present invention employing an inflatable balloon;

FIG. 17B is a side view of the invention of FIG. 17A with the inflatable balloon in its inflated state;

FIG. 18 is a side view of a further embodiment of the invention which uses an exhaust directing means;

FIG. 19 is a side view of another embodiment of the invention which uses an exhaust directing means;

FIGS. 20A and 20B are a top view and a side view, respectively, of an embodiment of the invention which is generally self-steerable;

DETAILED DESCRIPTION

Figure 1:
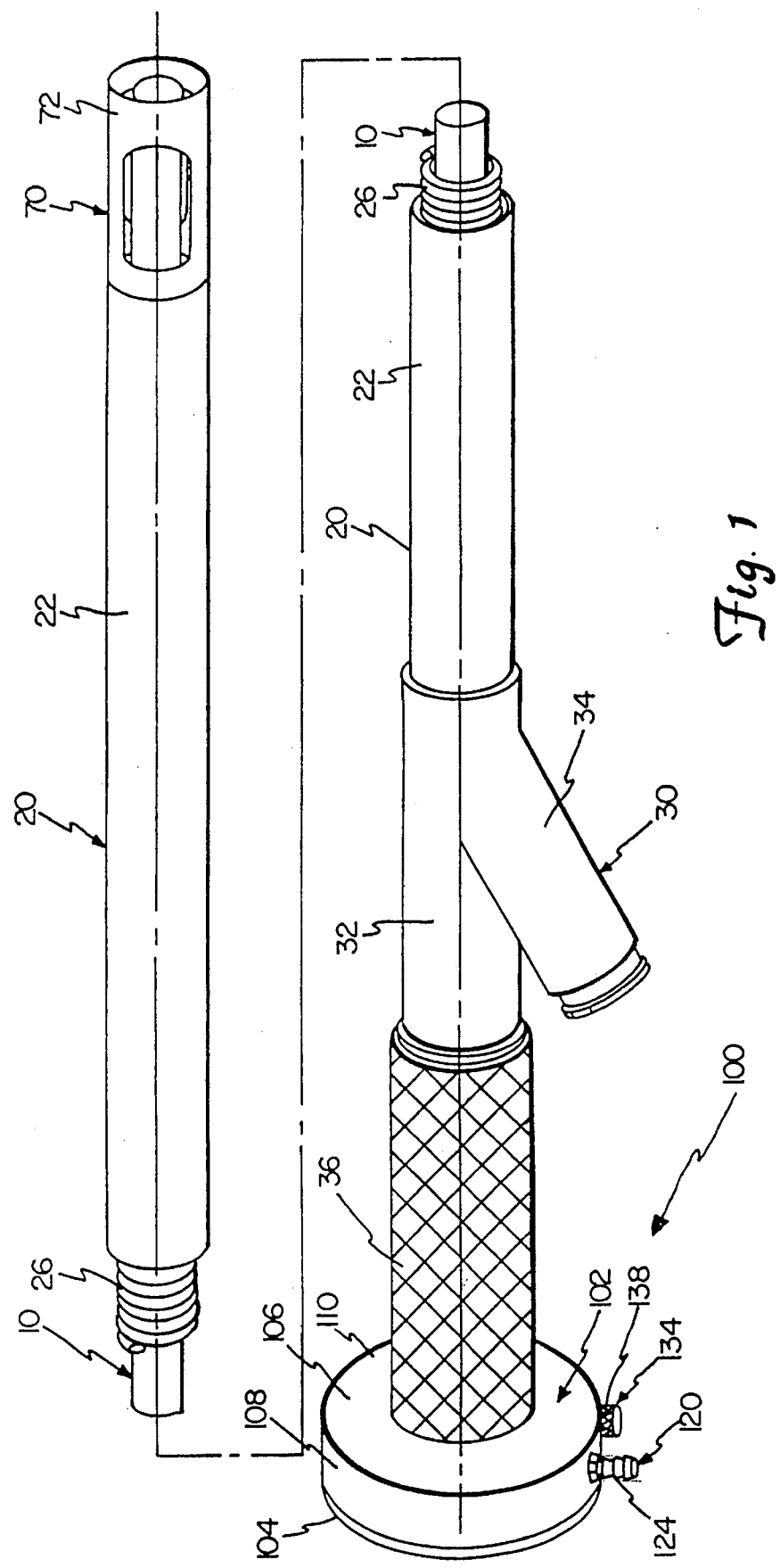
FIG. 1 is a perspective, partially broken away view of a medical device of the invention.

One preferred embodiment of a medical device of the invention is shown in FIGS. 1–4. This device generally includes an elongate, flexible shaft 10 carried within an elongate, generally tubular casing 20; a rotor 50 affixed to the shaft and carried within a rotor housing 70; and a drive means 100 operatively connected to the shaft for rotating the shaft.

Figure 7:
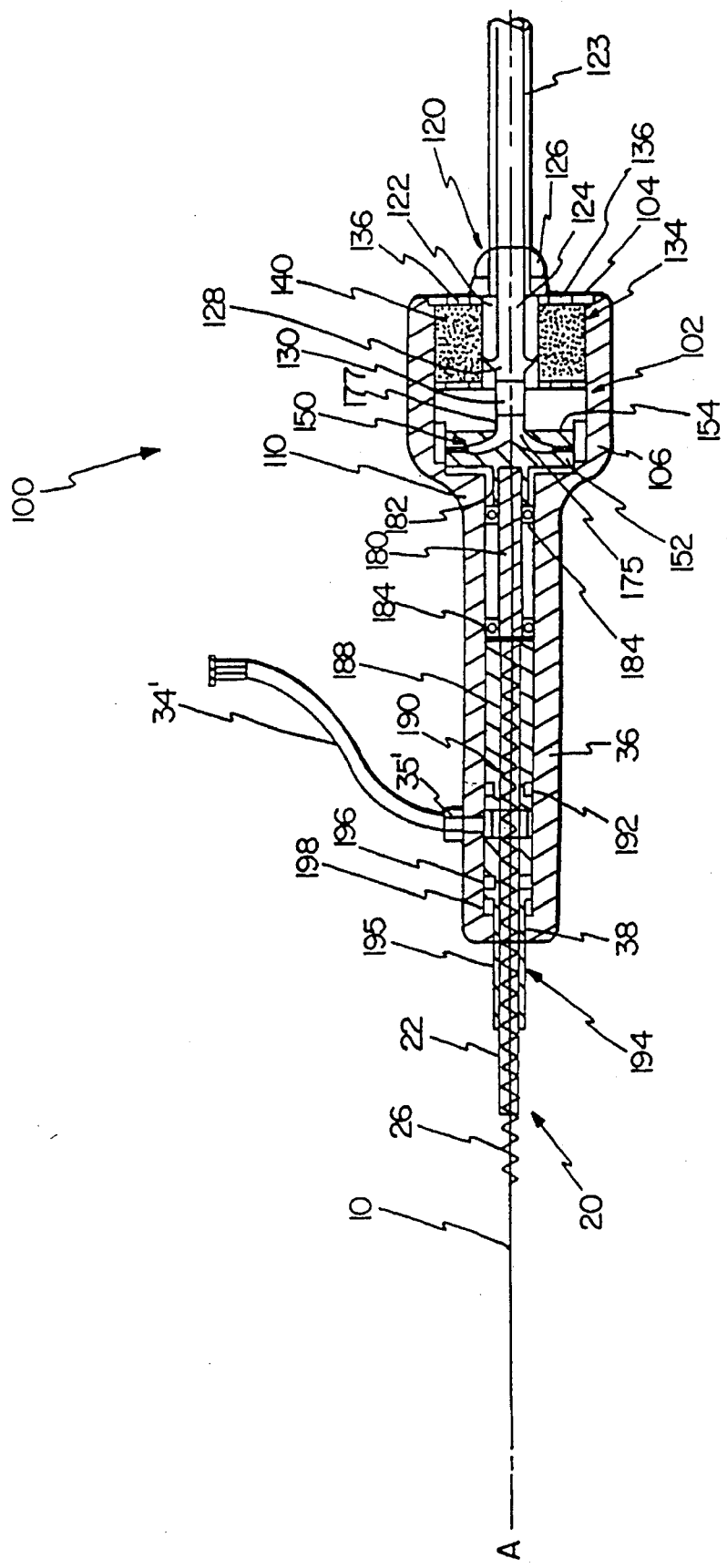
FIG. 7 is a cross-sectional view of a preferred drive means for use with the present invention.

The shaft 10 is elongate and generally cylindrical in shape and has a distal end 12 and a proximal end 14 (FIG. 7). The shaft is sized to be threaded, along with the rest of the device of the invention, along a vascular path within a patient's vascular system. The shaft will commonly have an outer diameter of between about 0.25 and about 1.5 mm, with a range of about 0.35 to about 0.65 mm being preferred. The length of the shaft can be varied fairly widely, depending upon the general types of locations within a vascular system intended to be accessed with the device. As a general rule, the shaft is desirably between about 50 cm and about 150 cm long, with a range of about 80 cm to about 100 cm providing a device which is useful for a wide variety of applications.

The shaft is desirably highly flexible so that it may be threaded through a patient's vascular system with ease. The shaft may be made of any of a wide variety of materials well known in the art, such as stainless steel. In one preferred embodiment, however, the shaft is formed of a shape memory alloy, such as a NiTi alloy. The use of such alloys in medical devices is known in the art and need not be discussed in great detail here. One important property of such alloys is that they exhibit superelasticity, i.e., they may be deflected to a much greater extent than most other metals, such as stainless steel before showing any permanent, plastic deformation. This property is explained in some detail in U.S. Pat. No. 4,926,860 (Stice, et al.), the teachings of which are incorporated herein by reference. In the present invention, this permits the shaft 10 to be guided along a tortuous vascular path without introducing a permanent "set" in the wire. Accordingly, when the shaft is guided to the desired location and rotated (as described below), its rotation will be centered almost exclusively about the axis of the shaft.

If a non-shape memory alloy, such as stainless steel, were used to form the shaft, the shaft would tend to take a permanent set, i.e., undergo plastic deformation, as it is guided along a tortuous vascular path. This would introduce a degree of curvature in the distal portion of the shaft 10. When the shaft is rotated, it will not rotate merely about its axis, but will also tend to spin somewhat wildly due to the curvature of the wire. If the shaft includes a rotor for degrading solid matter within the blood stream, this "whip" can readily lead to puncture of the vessel walls, as noted above.

In an alternative embodiment, the shaft 10 is formed of a "drawn-brazed strand" (DBS) cable. Most cables, particularly those used in medical applications, comprise a plurality of independent wire strands which are wrapped in a generally helical fashion about a central core wire. Although such a cable does tend to resist plastic deformation somewhat better than a single, unitary wire formed of the same material at the same diameter, the central wire strand of such a cable will tend to undergo plastic deformation to an extent proportional to that experienced by the larger diameter unitary wire. In a DBS wire of the invention, a plurality of separate strands are wrapped in a helical fashion, but no central wire strand is employed. By eliminating this central wire, the primary cause of "whip" is eliminated, thereby substantially eliminating whip in the shaft when it is subjected to rotation. Once the individual wire strands (not shown) of a DBS wire of the invention have been twisted about one another in a helical fashion, it is desirably drawn under pressure at high temperatures. As will be understood by those skilled in the art, this drawing and brazing of the wire can be used to meld the individual wire strands into a single wire having a larger diameter. Such a shaft generally appears the same as a solid wire, but the wire tends to retain some of the microstructure associated with the intertwined wire strands, yielding a wire with a tensile strength comparable to that of a cable. The individual wire strands used to form a DBS wire may be formed of any suitable material. As with the unitary, single strand shaft described above, the DBS shaft may also be formed of a shape memory alloy such as a NiTi alloy, if so desired.

FIG. 15 illustrates one particularly preferred embodiment of the shaft 10. The main body of the shaft may be as described above, but the shaft includes a weaker point along its length which will selectively structurally fail in the event of a malfunction. In the embodiment of FIG. 15, the shaft 10 is formed of two shaft segments 10A and 10B. these two shaft segments are joined together by a shear link 16. This shear link includes a reduced diameter portion where it joins the two links, defining a relatively weak area of the link. This reduced diameter portion should have a torsional strength less than that of the main body of the shaft so that will tend to break under torsional shear before the rest of the shaft will fail. This makes the device even safer in that the shaft will break at this link 16 when the shaft encounters undue resistance to turning, such as when there is some blockage of the rotor or some other unforeseen malfunction occurs.

The shear link 16 may be positioned at any suitable point along the length of the shaft. In the embodiment shown in FIG. 15, the link 16 is positioned almost immediately proximally of the housing 70. It should be understood, though, that the link 16 could be placed elsewhere, such as adjacent the joint between the shaft and the drive means 100 described below.

As noted above, the shaft 10 is desirably carried within a shaft casing 20. The shaft casing is desirably generally tubular in shape such that the shaft 10 may be retained and rotated within the casing. As shown in FIG. 1, the shaft casing 20 desirably extends along and encloses substantially the entire length of the shaft between the drive means 100 and the housing 70. The shaft 10 should be rotatable within the shaft casing so that, as the drive means 100 causes the shaft to rotate, the shaft casing 20 remains substantially stationary with respect to the drive means. The shaft casing should be flexible and sized to permit it to be threaded along a vascular path as the device of the invention is positioned within a patient's vascular system. In a preferred embodiment, the shaft casing comprises a tubular outer sleeve 22 formed of a biologically inactive polymeric compound, such as polyurethane or the like.

Figure 2:
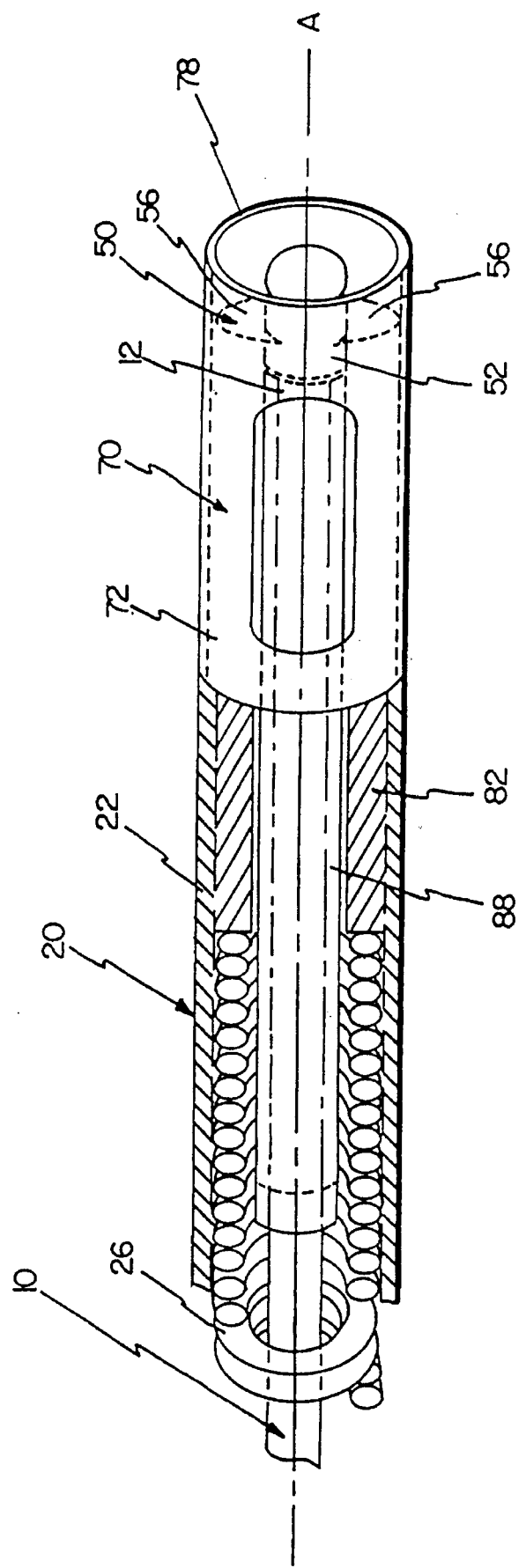
FIG. 2 is a perspective view in partial cross section of a distal portion of the device of FIG. 1.
Figure 6:
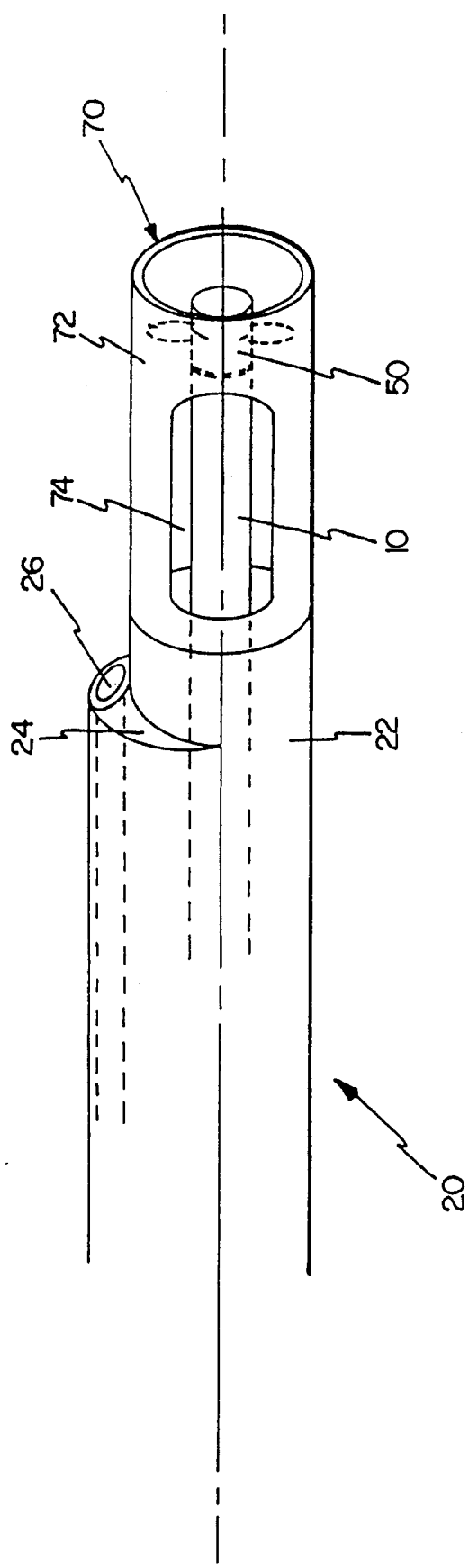
FIG. 6 is a perspective view of the distal portion of an alternative embodiment of the invention utilizing a guidewire tracking channel.

FIG. 6 depicts an alternative embodiment of the tubular outer sleeve 22 shown in FIGS. 1 and 2. In this embodiment, the outer sleeve is generally the same as described above in connection with FIGS. 1 and 2, but the outer sleeve further includes an arcuate projection which extends generally radially outwardly toward one side of the sleeve 22, as shown. This projection 24 includes a guide wire tracking channel 28 which may extend along substantially the entire length of the projection. This tracking channel permits one to simply direct a guide wire to the desired location within a patient's vascular system and then direct the distal end of the present invention to that location by passing the guide wire through the channel 28 so that the device follows the path of the guide wire accurately. The projection desirably terminates at a position proximally of the rotor housing 70 so that it does not interfere with the flow of fluid during operation of the device.

FIGS. 11A–11C illustrate an alternative embodiment of the invention utilizing a modified guidewire tracking channel 28'. In the embodiment shown in FIG. 6, the channel 28 is positioned in a projection 24 which extends along the casing 20. In FIGS. 11, though, there is no such separate projection, but rather the casing 20 is a dual lumen catheter having a larger inner lumen wherein the shaft 10 is disposed and a smaller second lumen which defines a guidewire tracking channel 28', with an inner wall 24' of the casing separating the two lumens. This tracking channel 28' extends along substantially the entire length of the casing 20, but terminates slightly proximally of the distal end of the device.

As best seen in FIG. 11C, the channel 28' tapers radially outwardly in a distal direction, leading a guidewire carried therein to relatively gradually slope radially outwardly until it is clear of the casing. In order to avoid too abrupt a change in the relative orientation of the guidewire and the casing where the guidewire exits the casing 20, the channel 28' tapers outwardly at a relatively small angle φ, which is desirably no more than about 35° and preferably between about 1° and about 5°. An embodiment having an angle φ of about 3° has been found to work well.

This tapering will define a generally elongate exit opening 27 in the casing where the guidewire is to exit the tracking channel 28'. The opening 27 may extend along both the distal segment of the casing 20 and a proximal portion of the rotor housing 70, as shown in FIGS. 11. In the embodiments which include one or more discharge ports 74 in the housing, as detailed below, the exit opening 27 is preferably disposed between the ports 74. This will help direct the distal portion of the guidewire between the ports and avoid any interference by the guidewire of the fluid flow established by the ports, which is explained below.

The guidewire tracking channels 28 or 28' shown in FIGS. 6 and 11 are useful when the device of the invention is to be deployed through a tortuous path or in performing a contralateral introduction. As such, this feature can be used with any of the other embodiments of the invention described herein. Hence, although the embodiments of FIGS. 6 and 11 illustrate rotor housings 70 which include a plurality of exhaust ports 74, it is to be understood that the guidewire tracking channel 28 or 28' can also be used with embodiments which do not include any ports 74 (e.g. the self-pumping version of the invention illustrated in FIG. 21).

In a particularly preferred embodiment, the shaft casing 20 includes an elongate inner bearing 26 disposed between the outer sleeve 22 of the casing and the shaft 10 to reduce friction between the outer sleeve and the shaft. In one embodiment, the bearing is desirably free-floating, i.e., it is not attached to any other element of the device, but rather is simply retained between the outer sleeve and the shaft. Although any of a wide variety of structures may be employed, one particularly useful design utilizes a helical coil, as shown in the drawings. Such helical coils are well known in the art and are most commonly used as structural elements of guide wires. They generally comprise an elongate wire strand, usually stainless steel wire, which is wrapped in a helical fashion about a mandrel and then removed from the mandrel.

In prior art devices wherein a rotating shaft is threaded through or carried within a catheter, a bearing generally is not employed. When the catheter and shaft of such a device are guided into position within a vascular system, the device almost always has to follow a curved path, and this path may include one or more relatively sharp angles. Where the path curves, the shaft tends to abut against the inner wall of the catheter, which defines the path which the shaft must take. When the shaft is rotated, there tends to be friction between the shaft and the catheter wherever such contact occurs. Not only will this friction obviously tend to generate heat, but it also introduces torsional strain in the shaft by providing resistance to rotation at the point of contact. Although these disadvantages may have only marginal deleterious consequences at lower rotational speeds, they tend to be problematic at higher rotational speeds. At higher speeds, the heat generated by friction could lead to localized areas of elevated temperature wherein the temperature is high enough to begin degrading the blood within the vascular system and/or the surrounding tissue of the vascular wall. Furthermore, the torsional strain placed on the shaft could well reach a level sufficient to cause catastrophic structural failure of the shaft.

By employing an inner bearing 26 between the shaft and the outer sleeve 22, one can minimize these adverse effects. Wherever a curve in the path of the device occurs, the shaft will abut against the bearing, which in turn bears against the outer sleeve 22, thereby avoiding direct contact between the rotating shaft 10 and the stationary sleeve 22. The free-floating bearing acts as a buffer between these two parts, minimizing friction. By reducing friction, the excess heat generated and the torsional strain placed on the shaft are both kept to a minimum. Furthermore, to the extent that friction introduces any undesired heat, the coil, which is generally formed of a metal such as stainless steel, will tend to act as a heat sink and more evenly distribute the heat to further minimize localized increases in temperature attributable to the friction. Accordingly, this reduces damage to blood and tissue as well as greatly reducing the likelihood of experiencing catastrophic failure of the shaft.

Although in the embodiment shown in FIGS. 1–10 the bearing 26 is free-floating, FIG. 14 illustrates another embodiment wherein the coil is fixed at at least one end. In the invention of FIG. 14, a coil is also used as the inner bearing 26, but the distal end of the coil is attached to the proximal end of the housing 70. The coil and the housing may be attached by, for example, a braze or solder joint 23; an adhesive material such as an epoxy could be used instead if so desired. For reasons outlined below, it is preferred that fluids be permitted to flow between the housing 70 and the shaft casing 20. Accordingly, the joint 23 between the coil 26 and the housing 70 should not define a fluid-tight seal between these two elements, but should instead simply structurally connect the coil to the housing.

If so desired, a standard "Y-type" connector may be attached to the outer sleeve 22 toward its distal end. These types of connectors are well known in the medical field and need not be discussed at great length here. Generally, though, they include a body portion 32 and an inlet tube 34. The body portion 32 is generally axially aligned with the outer sleeve 22 while the inlet tube 34 is angled distally outwardly from the body portion 32. The inlet tube 34 is in fluid communication with the interior of the shaft casing 20, permitting one to introduce any of a wide variety of fluids into the casing. In the embodiment shown in FIG. 9 (discussed at length below), the Y-type connector is replaced by an infusion line 34', which may be formed of a length of flexible tubing or the like. The infusion line may be affixed to the sleeve 36 of the housing of the drive means 100 by means of a Luer fitting 35' or the like. Like the inlet tube 34 of the Y-type connector, the infusion line 34' is in fluid communication with the interior of the shaft casing 20.

Fluids which may commonly be used in connection with the present device include saline solution, contrast medium (for enhancing the radiographic visibility of the device) and fibrinolytic solutions (for medically breaking down fibrin, a major component of most thrombi). When such a fluid is introduced through the inlet tube (FIG. 1) or infusion line (FIG. 7) and injected into the shaft sleeve, it will tend to flow out of the distal end thereof. This flow of fluid tends to act as a lubricating and cooling medium to further reduce the undesirable effects caused by friction as the shaft is rotated.

A rotor 50, which may also be referred to as an "impeller," is affixed to the shaft 10 adjacent the distal end thereof for rotation therewith. As best seen in FIG. 4, the rotor 50 generally includes a central body 52 having at least one blade 56 carried thereon. The central body 52 is desirably generally tubular in shape, having a cylindrical aperture 54 extending through the body along the axis thereof. As explained in more detail below, this aperture 54 is intended for receiving a portion of the shaft 10 adjacent its distal end 12. Any number of blades 56 may be carried about the central body 52. In the preferred embodiments shown in FIGS. 2 and 4, the rotor 50 includes a pair of generally diametrically opposed blades 56 which extend generally radially outwardly of the central body 52. In the embodiment shown in FIG. 2, each of the blades is semi-elliptical in shape and is positioned diametrically opposite the other blade. Each blade is desirably positioned within a plane which obliquely intersects the axis A of the shaft, and the opposite blade is substantially a mirror image of the first blade. This construction is not unlike that of the propeller of a prop-style airplane, the oblique orientation of the blades 56 causing fluid to be thrust generally axially rearwardly of the rotor when the rotor is caused to rotate.

A particularly preferred embodiment of a rotor of the invention is shown in FIGS. 4A and B. In this embodiment, as in the previous one, the blades extend generally radially outwardly of the body 52 from diametrically opposite locations. However, in this "screw type" rotor, each blade spirals in a generally helical fashion along the length of the body. In the embodiment shown, each blade extends about approximately 180° of the circumference of the body 52 between the blade's proximal 58 and distal 60 ends. The rate at which the blade 56 follows around the circumference of the body along its length can be varied as desired. In one embodiment which is found to be particularly useful, a plane within which a segment of the blade lies is oriented at an angle theta ($\theta$) of approximately 40° from a plane orthogonal to the axis A of the body 52.

As noted above, one of the major components of most thrombi is fibrin. As the name implies, fibrin is generally formed of elongate strands of a proteinaceous material. When the rotor 50 is rotated within a vascular channel to break up a thrombus, fibrin will tend to become wrapped around the body 52 of the rotor if the rotor is not accelerated from an initial stationary position to full rotational speed quickly enough. As described in more detail below, the drive means 100 of the invention is intended to permit sufficient torque to be applied to the shaft 10 to reach maximum rotational speed rather quickly to avoid this problem.

If so desired, a sharpened leading edge 62 may be provided adjacent the distal end 60 of each blade 56. In this embodiment, the leading edge of the blades do not lie in a plane orthogonal to the axis A of the body 52 as do the trailing edges 64 at the proximal end 58 of the blades. Instead, the leading edge lies within a plane which is angularly displaced from an orthogonal plane through an angle alpha. This angle alpha is desirably between about 30° and about 60°, with a range of between about 40° and about 45° being preferred. This provides a sharp, acute angle at the distal end of the blade, permitting the sharpened distal edge of the blade to slice the fibrin before it can become twisted about the rotor.

The rotor may be affixed to the shaft by any suitable means. In a preferred embodiment, a distal portion of the shaft 10 is received within the aperture 54 formed in the body 52 of the rotor. The shaft may then be permanently adhered to the rotor in any desirable fashion, such as by brazing or by means of a curable, biologically inert cementitious material.

A thrombectomy device of the invention also includes a rotor housing 70 carried about the rotor and within which the rotor rotates. The housing comprises a generally cylindrical wall 72 having an inner diameter greater than the outer diameter of the rotor 50 so that the rotor may freely rotate within this housing. In a particularly preferred embodiment, the inner diameter of the housing 70 is only slightly greater than the outer diameter of the rotor 50. This close proximity between the rotor and the wall 72 of the housing increases the shear force applied to a fluid passing through the housing as the rotor is rotated. This heightened shear force will serve to further break up the thrombus carried within the blood, permitting the rotor to more rapidly degrade a thrombus entrained in the fluid into sufficiently small particles. The axis $A_H$ of the housing 70 is desirably substantially aligned with the axes of the rotor 50 and shaft 10.

The rotor housing 70 includes a plurality of ports 74 which pass through the cylindrical wall 72. For reasons explained in more detail below, the ports are desirably spaced equiangularly about the circumference of the housing. The rotor 50 is desirably positioned generally toward the distal end 78 of the housing, as shown in FIG. 2. In a particularly preferred embodiment, the ports 74 are positioned about the wall 72 of the housing immediately distally behind the rotor 50.

When the rotor is rotated within a blood vessel, the blood therein will tend to be thrusted generally proximally by the rotor, as noted above. This creates a pressure differential between the area immediately forward of the rotor and that immediately behind the rotor, with the pressure behind the rotor being significantly greater than that immediately in front of the rotor. This increased pressure behind the rotor increases the pressure within the housing, and blood is therefore ejected through the ports 74. As the ports are positioned about the cylindrical wall slightly behind the rotor, the blood passing therethrough exit the housing 70 relatively close to the distal end 78 of the housing. The low pressure adjacent the distal end of the rotor tends to draw the blood being expelled through the ports back through the rotor, thereby creating a recirculating vortex wherein a substantial portion of the fluid exiting through the ports tends to pass through the rotor repeatedly.

When a thrombus is drawn into the housing by the rotor, the rotor will tend to divide it into a number of smaller particles, which may well remain too large. However, these particles will be entrained in the blood expelled through the ports and will therefore tend to be drawn back into the rotor and become degraded even further. After a sufficient number of passes through this recirculating vortex, the thrombus may be broken into a large number of very small, discrete particles. These particles may be made small enough to substantially eliminate the risk that they would tend to cause blood to coagulate about them again to produce additional thrombi or cause any distal embolization.

When in use, the rotor will usually be positioned within the confines of a vascular channel adjacent the location, or suspected location, of a thrombus. When the rotor is rotated and causes blood to be ejected through the ports 74, the ejected fluid will impinge upon the vascular wall, tending to urge the housing away from the vascular wall as a reaction to this impinging fluid. If each of the three or more equiangularly spaced ports are of substantially the same size, the fluid volume passing through each port and the rate at which the fluid is expelled from the ports will be substantially equivalent. Accordingly, the reactionary force acting against the housing to urge the housing away from the vascular wall will become equalized when each of the plurality of equiangularly spaced, similarly sized ports are approximately the same distance away from the vascular wall. Thus, the fluid flowing through the ports in the housing will tend to automatically center the housing and the rotor within the vascular channel when the rotor rotates.

If a force is applied to urge the housing away from its centered location, e.g., if the shaft 10 is deformed and begins to "whip," the force associated with the blood being expelled through the ports will tend to rapidly urge the housing away from the vascular wall. Thus, the housing will not only automatically be centered when in use, but it will tend to remain centered within the vascular channel. If only two ports are utilized (as in the device shown in FIG. 1), though, the housing may not remain centered. The fluid expelled through the two diametrically opposed ports will tend to ensure that the housing remains equally spaced from portions of the vascular wall along a line passing through both of the ports, i.e., in a horizontal plane in FIG. 1. However, if a force tends to urge the housing in a direction other than along that line (i.e., upwardly or downwardly in FIG. 1), the fluid will not be expelled in a direction which would permit it to counteract this displacement and urge the housing toward the center of the vessel. Hence, the use of three or more equiangularly spaced ports is preferred due to its ability to cause the housing to remain centered within the vascular channel.

Figure 3:
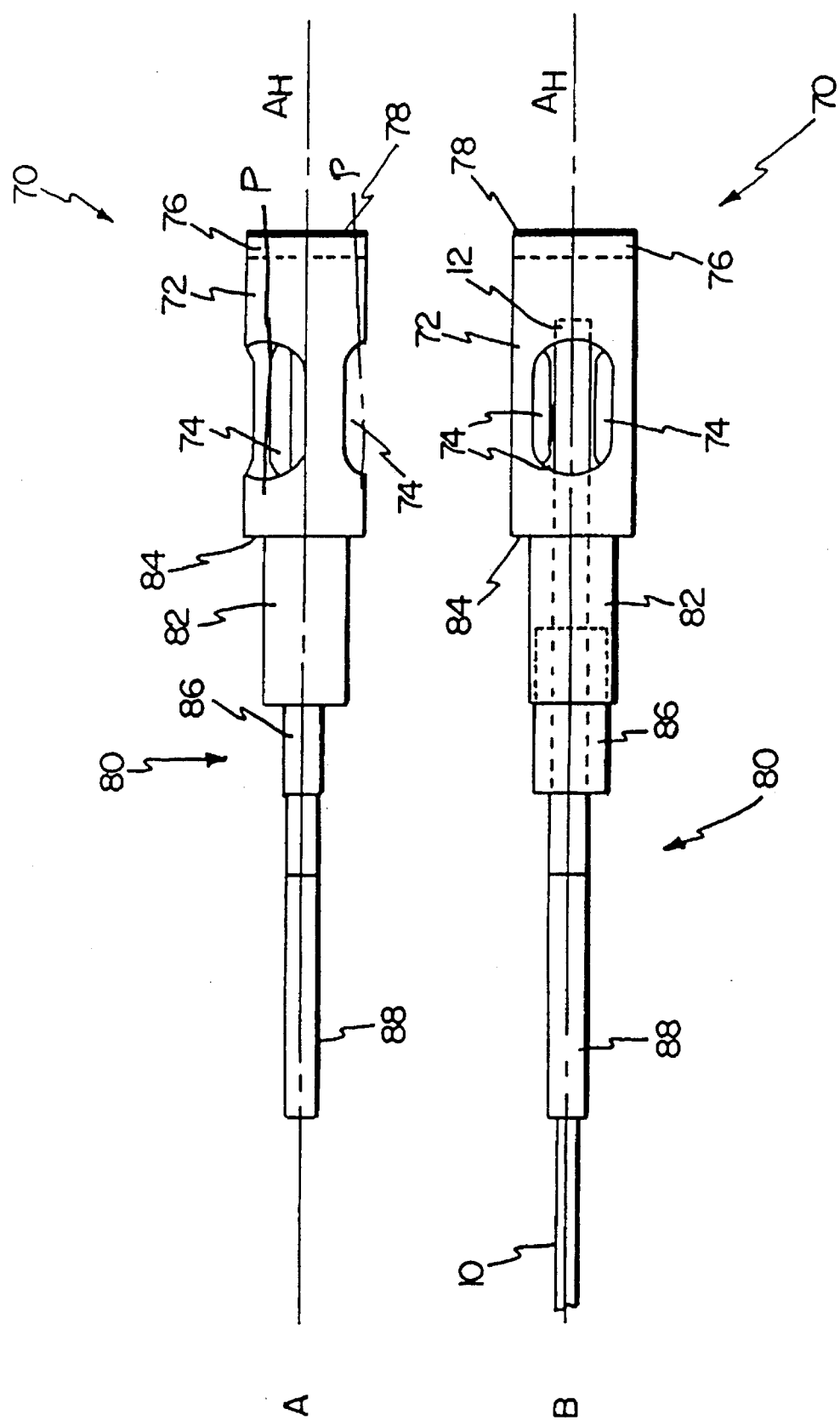
FIG. 3 is a side view and a top view of the rotor housing of the device of FIG. 1.

FIG. 12 shows a modification of the ports shown in, e.g. FIG. 3, which has been found to further optimize the recirculation of the fluid flowing through the housing 70. As shown in FIG. 3, the major axes P of the generally elliptical ports 74 in that embodiment are generally parallel to the axis $A_H$ of the generally cylindrical wall 72 of the rotor housing.

In the embodiment illustrated in FIG. 12, though, the major axes P of the ports are disposed oblique to the axis $A_H$ of the housing. Although the major axes P of the ellipses are technically arcuate and wrap about the axis $A_H$ of the housing, the degree of offset between the generally parallel axes P of the ports can be expressed as an angle σ, as shown. An angle σ of about 20° to about 45° has been found to help direct the fluid exiting the housing through the ports 74 toward the distal end of the housing, making the recirculating vortex of fluid more efficient and ensuring even more thorough maceration of the thrombi entrained therein in the same amount of time.

FIG. 13 illustrates an alternative embodiment of the invention which utilizes a multi-stage rotor design. In FIG. 13, the single rotor 50 of the embodiments discussed above is replaced with a series of individual rotors 50A, 50B and 50C. Each of these rotors may be shaped generally as outlined above and are each attached to the same shaft 10 for rotation therewith. The housing 270 of this embodiment is elongated to accommodate all three rotors. Although the housing 270 may be formed entirely of metal or the like, having such an elongated, rigid housing may impair the ability to guide the rotors to a site in a patient's vascular system which may require following a tortuous path. Hence, in the embodiment shown, the elongate, generally cylindrical wall 272 of the housing 270 is optimally formed of a flexible material, such as a polymeric material commonly used in forming catheters. In particular, the invention of FIG. 13 utilizes a distal segment of the casing 20—which may be a catheter, as noted above—as the wall 272 of the housing.

In order to ensure that the rotors 50A–50C do not impinge directly against the relatively soft wall 272 and the make sure that the rotors are properly centered in the housing, each rotor may be provided with a separate sub-housing 280A–280C which encloses the rotor. Each sub-housing 280 includes a generally cylindrical wall 282, which may be formed of metal or the like, received within the more flexible wall 272 of the main housing 270. This wall 282 of the sub-housing is optimally adapted to fit relatively snugly within the lumen of the main wall 272 to limit relative movement of these walls.

Each sub-housing also includes a forward strut 284 and a rearward strut 286, with each strut having a rotation sleeve 288 for rotatable receiving the shaft 10 therethrough. These struts serve to provide structural support to the sub-housings 280 and passing the shaft 10 through the sleeves 288 in these struts serves to fix the relative positions of the sub-housings and the shaft. Furthermore, since the rotors 50A–50C are affixed to the shaft, the sleeves 288 also serve to position the rotor within the sub-housing assemblies, both centering the rotor within the circumference of the wall 282 and preventing any undue axial movement of the rotors within the sub-housings.

As with the single-rotor design described above, the first rotor 50A can simply draw fluid in through the distal end of the housing. If so desired, only a single set of exhaust ports 274 may be provided adjacent the distal end of the housing 270. These exhaust ports 274 are desirably spaced generally equiangularly about the circumference of the housing 270 and serve much the same functions as the ports 74 in the embodiments outlined above, e.g. assisting recirculation of the fluid past the rotors and helping to center the housing within a vessel.

In a particularly preferred embodiment, though, the sub-housings 280A–280C and their associated rotors 50A–50C, respectively, may be thought of as effectively defining three separate maceration zones. Exhaust ports 274 are positioned at the rearward end of each of these zones, i.e. at a location spaced slightly proximally of the associated rotor. In the embodiment shown in FIG. 13A, these exhaust ports 274 are positioned rearwardly of the sub-housing 280 and need only extend through the cylindrical wall 272 of the main housing 270. A set of equiangularly spaced intake ports 276 is also provided for each of the two proximally spaced rotors, 50B and 50C, with the intake ports 276 being positioned generally distally of the associated sub-housings 280B and 280C, respectively. In the embodiment shown, each set of exhaust ports 274 and each set of intake ports 276 comprises four equiangularly spaced ports, with the exhaust and intake ports being axially aligned so that one intake port will be positioned immediately distally of the adjacent exhaust ports.

The main path of fluid flow is schematically depicted by arrows in FIG. 13A. In this embodiment of the invention, the distal rotor 50A will draw fluid into the housing 270 through the open distal end of the housing. After the fluid passes over the first rotor, it will tend to exit the housing through the exhaust ports 274. A substantial portion of the expelled fluid will then reenter the housing through the intake ports 276 for maceration by the second rotor, 50B while the remainder of the expelled fluid will be drawn back toward the distal end of the housing for another pass by the first rotor 50A. The fluid will once again exit the housing 270 through exhaust ports 274 positioned behind the sub-housing 280B and reenter the housing through intake ports 276 disposed in front of the third rotor 50C. Finally, fluid will exit the housing through the last set of exhaust ports 274 stationed proximally of the third sub-housing 280C.

By allowing the fluid to exit the housing and reenter rather than simply being thrust proximally through the housing until it is exhausted through a single set of ports, one can establish three separate recirculating vortexes, with a portion of the fluid exiting each rotor being passed rearwardly for maceration by the next rotor and another portion of the fluid being recirculated back into either the distal end of the housing or the previous intake ports 276 for another pass over the same rotor.

If so desired, optional bulkheads 290 (shown in phantom lines in FIG. 13A) may be positioned between the rotors.

These bulkheads may be relatively thin struts such as the struts 284, 286 of the sub-housing assemblies and be utilized simply to support the relatively flexible wall 272 of the main housing to prevent it from being inadvertently drawn into one of the rotor housings 280B, 280C during operation. Alternatively, the bulkheads may be present a larger surface area, e.g. generally disc-shaped bulkheads having centrally located openings through which the shaft may pass. Such wider bulkheads would tend to restrict the flow of fluid through the housing 270, thereby limiting the amount of fluid that flows directly from one rotor to the other within the lumen of the housing without exiting through the exhaust ports 276 and reintroduced through the intake ports 276. The bulkheads, particularly in this embodiment, are ideally placed between adjacent sets of exhaust ports 274 and intake ports 276, as shown.

Figure 5:
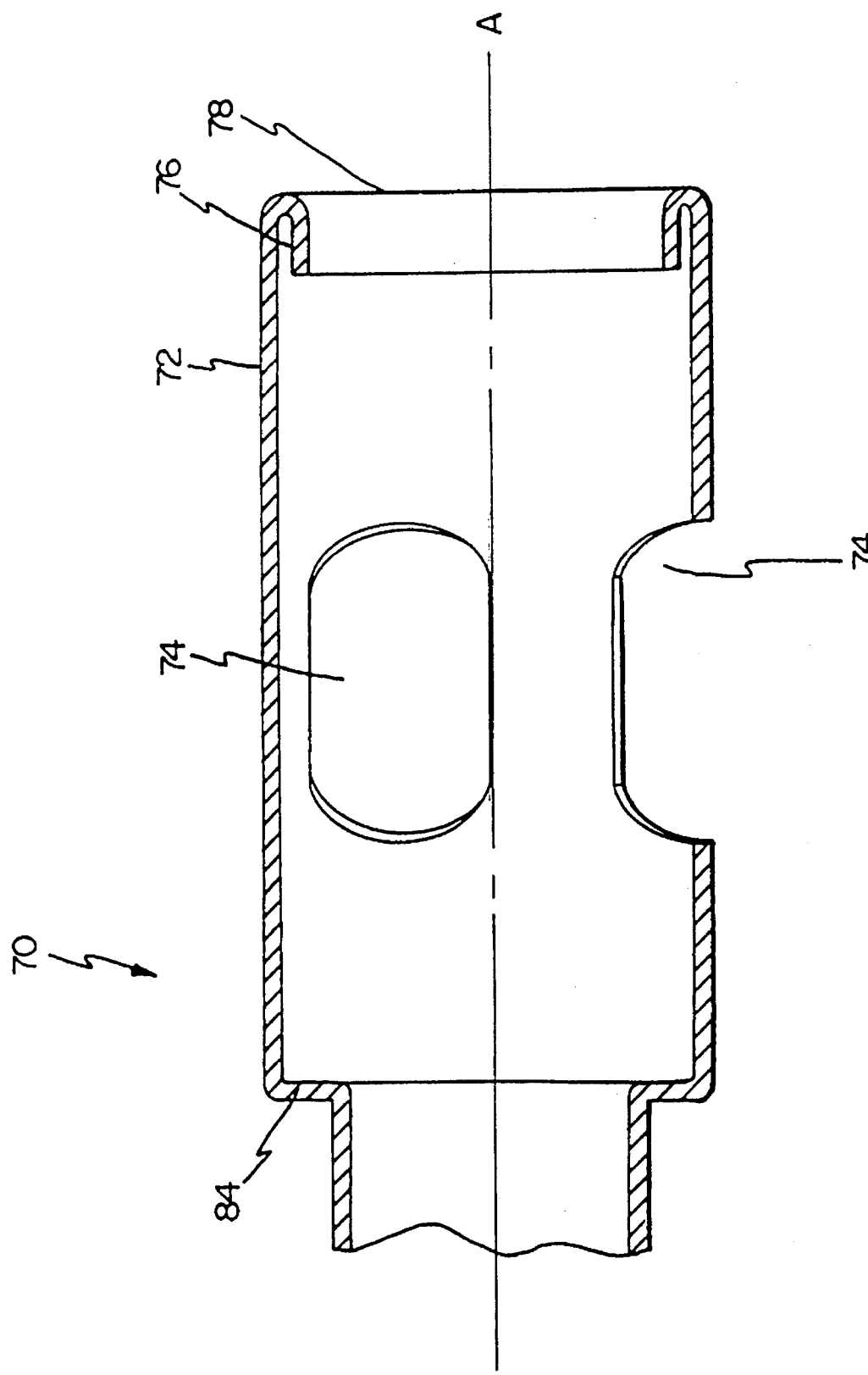
FIG. 5 is a cross-sectional view of a preferred embodiment of a rotor housing of the invention.
Figure 8:
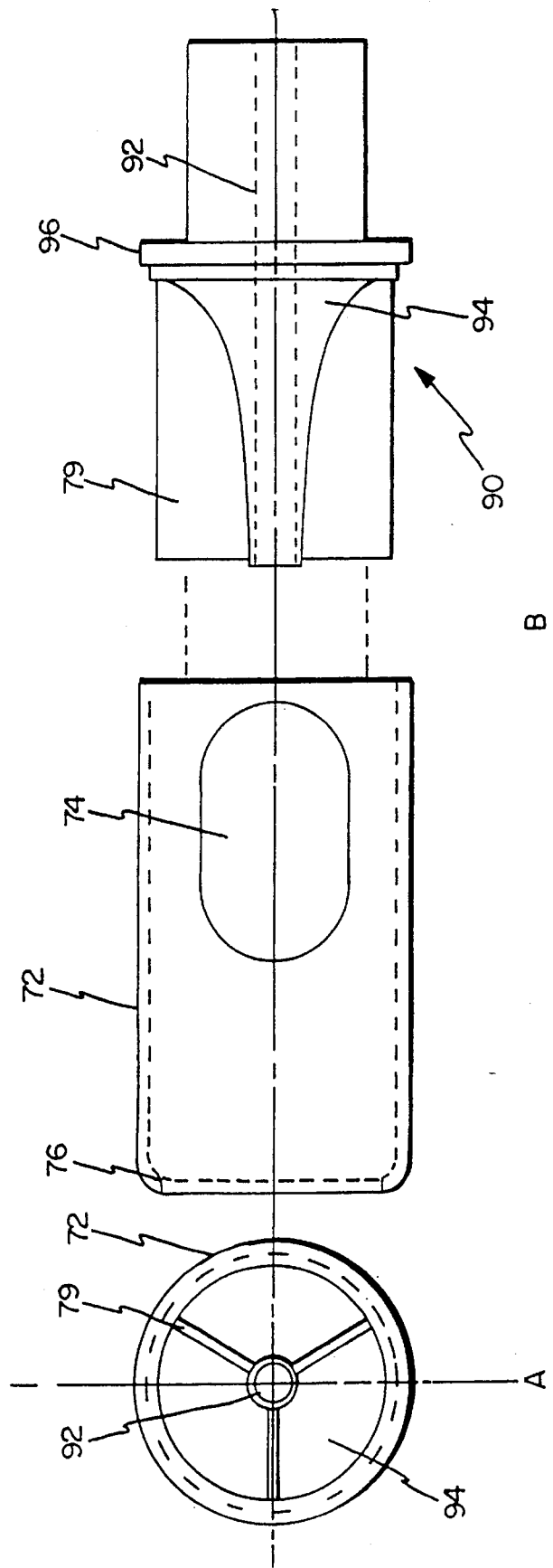
FIG. 8 is an end view and an exploded side view of an alternative embodiment of a rotor housing of the invention.

As best seen in FIGS. 5 and 8, the housing 70 may be provided with a generally inwardly extending distal bead 76 adjacent its distal end. This distal bead is desirably rounded to provide the housing with a rounded distal end 78 for contacting tissue as the device is deployed within a vascular system. The distal bead may be formed on the housing by inwardly deforming a distal portion of the cylindrical wall to form an annular bead disposed within a distal segment of the housing. Two possible bead constructions are shown in FIG. 5, which depicts one useful shape, and FIG. 8, which shows an alternative embodiment of such a bead. Such a rounded distal end 78 tends to be less traumatic than either the more blunt distal end 78 shown in FIG. 2 or an exposed rotor 50 which is not surrounded by a housing, as is most common in the prior art.

As noted above, this distal bead 76 is desirably generally inwardly extending, though it may also extend outwardly of the cylindrical wall 72 of the housing. The inner diameter of the housing adjacent its distal end, i.e., adjacent the distal bead 76, is desirably less than the maximum outer diameter of the rotor 50. This serves as a further safety measure in that if the shaft 10 breaks, the rotor will be unable to pass through the distal end of the housing. This prevents the rotor and a broken off distal portion of the shaft from becoming left within the blood stream of the patient if the shaft does indeed fail.

FIG. 16 shows an alternative embodiment of a distal end 78 of a housing for use with the invention. In the embodiments discussed immediately above, the housing was provided with a rounded tip by means of a distal bead 76 formed integrally with the housing. In FIG. 16, though, the distal bead 76' is formed of a relatively soft polymeric material, such as by molding the bead from a plastic commonly used in forming catheters and the like. The distal end of the cylindrical wall 72 of the housing desirably tapers inwardly to form a restrictive flange 75, to which the distal bead 76' may be attached. This flange 75 desirably extends inwardly sufficiently to ensure that the distal end of the housing has a smaller diameter than the diameter of the rotor 50 to ensure that the rotor will be retained within the housing in the case of a broken shaft or the like.

FIG. 8 depicts an alternative construction of the housing 70 of the invention. In the embodiment shown in FIGS. 3A and B and FIG. 5, the housing is desirably integrally formed of a single, unitary piece of material, such as surgical stainless steel. In the embodiment shown in FIG. 8, however, the housing 70 is formed of two separate elements which can be affixed to one another when assembling the invention. The cylindrical wall 72 which is carried about the rotor forms a first, distal element which can be permanently attached to the other, proximal segment 90 by any suitable means, such as by brazing. The proximal segment 90 has a central aperture 92 extending centrally therethrough for rotatably receiving the shaft 10 to position a proximal portion of the shaft and the rotor attached thereto in the center of the cylindrical distal segment 72.

A plurality of fins 79 (described in more detail below) are positioned equiangularly about a generally frustoconical housing insert 94. The insert 94 and the fins are sized to be closely received within the confines of the cylindrical wall 72 when the housing is assembled. The insert desirably tapers radially outwardly in a proximal direction from an initial outer diameter only slightly greater than that of the shaft 10 to an outer diameter adjacent its proximal end generally equal to the inner diameter of the cylindrical wall 72. Although this taper may be generally linear, in the preferred embodiment shown the rate of taper is much greater adjacent its proximal end. This directs fluid being thrust proximally through the housing radially outwardly through the ports 74, reducing the tendency of fluid exiting the housing to flow in a proximal direction, so that the fluid may be drawn back into the recirculating vortex explained above.

An annular abutment 96 may be provided adjacent the proximal end of the housing insert 94. This abutment has an outer diameter greater than the inner diameter of the cylindrical wall 72 and thus serves to abut the proximal end of the wall when the housing is assembled. If so desired, the wall 72 may be affixed directly to this abutment. In a particularly preferred embodiment, the outer diameter of the abutment 96 is substantially equal to that of the cylindrical wall to provide the housing with a smooth outer surface.

As noted above, the housing insert 94 may include a plurality of fins 79 positioned equiangularly about its circumference. The number of fins employed is desirably equal to the number of ports 74 in the housing, and one fin may be positioned immediately adjacent each port. If so desired, the fins may be parallel to the major axis of their respective, generally elliptical ports. When the device is assembled, the rotor 50 will be positioned distally of the housing insert 94; the fins will therefore be positioned proximally of the rotor. As fluid is thrust proximally within the housing 70 by the rotor, it must pass over the fins before exiting the housing. Any solid matter, such as a thrombus, entrained within the fluid will strike the fins, which form a part of the housing and are thus stationary with respect to the spinning rotor. Solid matter will tend to be broken up when it impacts the fins, so the fins serve to speed up the degradation of thrombi or the like within the fluid.

A connector 80 may extend proximally of the cylindrical wall 72 of the rotor housing 70 and permit the housing to be attached to the distal end of the shaft casing 20. The connector 80 includes a first segment 82 adjacent and connected to the cylindrical wall 72 of the housing. The outer diameter of this first segment 82 is desirably substantially equal to the inner diameter of the outer sleeve 22 of the shaft casing adjacent its distal end so the first segment 82 may be closely received within and retained by a distal portion of the outer sleeve 22. The outer diameter of the cylindrical wall 72 of the housing is desirably substantially equal to the outer diameter of the shaft casing 20 to present a relatively smooth outer surface at the junction between the housing and the shaft casing. The decrease in diameter between the cylindrical wall 72 and the first segment 82 may be relatively abrupt, defining a generally rearwardly facing annular shoulder 84 for abutting the distal end of the outer sleeve 22. In order to ensure that the housing is firmly affixed to the shaft casing, the first segment 82 may be cemented to the lumen of the outer sleeve by means of an epoxy or the like (not shown).

The connector 80 may also include a second segment 86 which is disposed proximally of the first segment 82 and is attached thereto. The maximum dimension of this second segment is desirably larger than the inner diameter of the inner bearing 26. The second segment thus serves to distally limit the axial movement of the inner bearing and serves to retain the bearing in place about the shaft 10 within the outer sleeve 22.

In a particularly preferred embodiment, the second segment 86 is generally rectangular in cross section, as indicated in FIGS. 3A and B, rather than being generally cylindrical. The second segment may be substantially solid in cross section, but includes a central aperture passing therethrough for receiving the shaft 10. The axis of this cylindrical aperture is preferably substantially aligned with the axis of the shaft and the aperture is sized to permit the shaft to freely rotate therein. The second segment thus serves to support the shaft in a spaced relationship with respect to the shaft casing 20 and helps to ensure that the rotor is axially centered within the cylindrical wall of the housing rather than abutting against the wall. Utilizing a generally rectangularly shaped second segment having maximum dimensions less than the diameter of the first segment 82 provides a space between the second segment and the shaft casing 20. This space allows fluids, such as the contrast mediums or fibrinolytic solutions noted above, to pass distally from within the casing through the housing and into the vascular channel.

FIG. 10 depicts an alternative embodiment of a rotor housing 70 and connector 80 of the invention. In this embodiment, the connector does not include a second segment 86 disposed rearwardly of the first section 82. Instead, a coiled support member 86' is utilized. The support member 86' is carried within the first segment 82 and extends along the length thereof from a position adjacent the annular shoulder 84 to the proximal end of the first segment. The support member desirably comprises a widely spaced helical coil formed of a wire having a diameter adapted to extend radially inwardly of the first segment a sufficient distance to provide lateral support to the shaft 10 carried within the helical coil. The axes of the shaft, the first segment and the helical support member 86' are desirably substantially aligned with one another.

Adjacent turns of the helically coiled wire are desirably spaced apart from one another. This permits fluid to pass through the support member 86' at relatively high flow rates as the space between the adjacent turns effectively defines a generally helical path along which fluid may freely flow between the interior of the shaft casing 20 and the rotor housing 70. The direction of this fluid flow is schematically represented by arrows in FIG. 10 and, as indicated by the bi-directional character of these arrows, fluid may flow in either direction along this helical channel—if one is aspirating fluid from within the vascular channel, the fluid would flow generally proximally, while fluid would flow generally distally if one were delivering a fibrinolytic solution or the like into the vessel through the shaft casing.

Figure 22A:
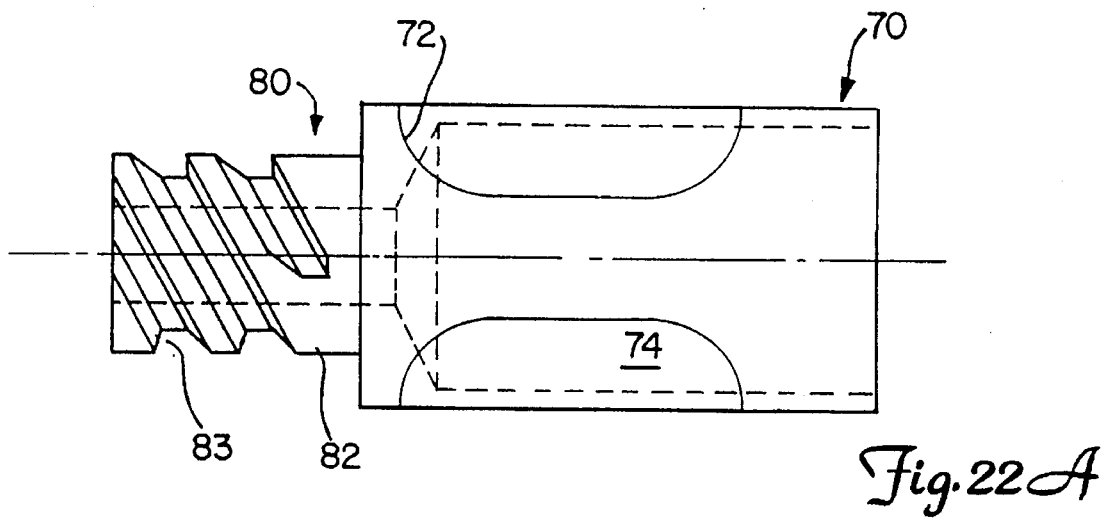
FIGS. 22A and 22B are top and side elevational views, respectively, of another embodiment of the invention which is generally self-steerable.
Figure 22B:
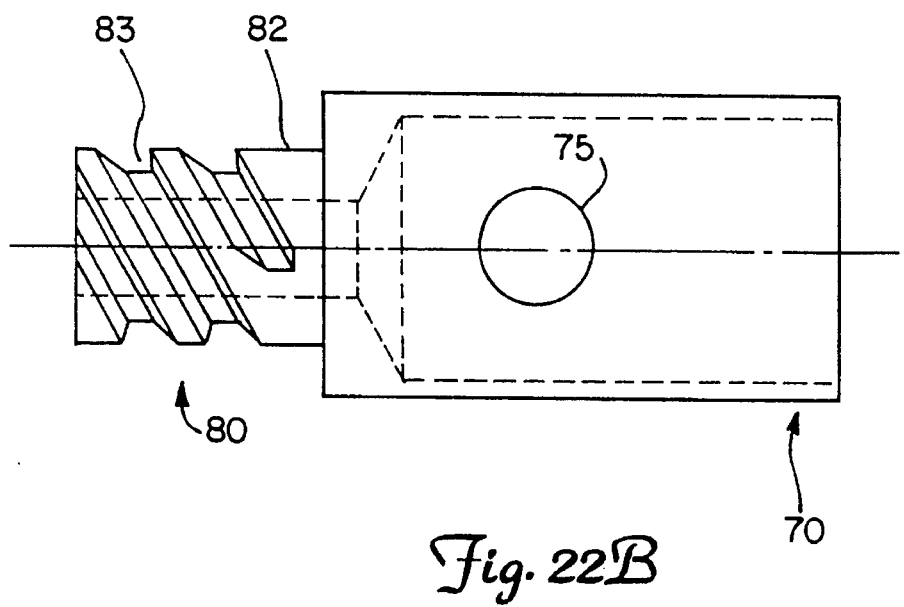

FIGS. 22A and 22B illustrate yet another embodiment of the housing 70 and connector 80 of the invention. In this embodiment, the first section 82' is adapted to be directly connected to the bearing 26 (not shown in FIG. 22) within the casing 20. The first section 82' has a generally helical slot 83 extending about its surface. This slot 83 should be adapted to receive a distal portion of the bearing, which is desirably a helically would coil, as noted above. The pitch of the coil should be adapted to permit the coil to be readily threaded into the helical slot 83 in the connector 80. If so desired, the bearing 26 can then be affixed to the connector 80, such as by brazing the coil to the connector or connecting these elements with a suitable adhesive. When assembled, this connection between the bearing and the connector may have an appearance substantially as shown in FIG. 14 and described above in connection with that drawing.

The connector 80 of the housing is desirably also provided with a shaft support sleeve 88 for supportingly receiving a portion of the shaft adjacent its distal end. The support sleeve 88 may be of any desired construction, but preferably comprises a thin-walled stainless steel tube, known in the art as a "hypotube," having a length of between about 0.25 and about 0.35 inches. The sleeve is sized to permit the shaft to rotate freely therein, yet limit lateral movement of the shaft so that it may stabilize the shaft in a position wherein the axis of its distal portion is substantially aligned with the axis $A_H$ of the housing. The support sleeve 88 may extend distally through the first 82 and second 86 segments of the housing (or the first segment 82 and the support member 86' in the embodiment of FIG. 10) to a position within the rotor housing 70 immediately adjacent the rotor 50 (as best seen in FIGS. 2 and 10).

FIGS. 17–19 illustrate embodiments of the invention which utilize fluid directing means to direct fluid exiting through the exhaust ports 74 back toward the distal end of the housing for further maceration. This serves to further ensure that fluid will be efficiently recirculated toward the distal end of the housing to ensure that any thrombi present are thoroughly macerated. The fluid directing means is optimally expandable from a collapsed state useful for deployment of the invention in a patient's vascular system to an expanded position wherein it is directing fluid for recirculation.

In the embodiment of FIGS. 17A and 17B, a balloon serves as the fluid directing means. The casing 220 of this invention provides a selectively inflatable balloon 222 about a distal section 224 of the casing. This "balloon catheter" includes a separate inflation lumen 226 through which an inflation fluid may be passed and ports 228 deliver fluid from the inflation lumen 226 to the interior of the balloon 222 to inflate the balloon. The balloon may also be deflated in mush the same fashion, with the fluid being withdrawn from the interior of the balloon through the inflation lumen 226 via the ports 228. Such "balloon catheters" are well known in the art and need not be discussed at great length here.

In using the present invention, the device will be positioned in a patient's vascular system at the desired location for treatment. The balloon can then be inflated until it engages the sidewall of the vessel, substantially filling the lumen of the vessel. The balloon may be inflated with any suitable fluid which may be subsequently withdrawn to deflate the balloon so that the device can be withdrawn when the operation is complete. It is particularly desirable to use a fluid which is biocompatible, e.g. a radiopaque contrast medium or a saline solution, so that no harm will be done to the patient if the balloon accidently ruptures.

The inflated balloon 222 serves two functions. First, fluid will be effectively prevented from travelling proximally beyond the balloon. As the fluid is ejected from the exhaust port or ports 74 it will be readily drawn back up to the distal end of the housing for another pass over the rotor, promoting the recirculation of the fluid to thoroughly degrade any thrombi entrained in the fluid. This can be particularly helpful in situations where the risk of even relatively small thrombi being left after the procedure is higher than normal, as in cardiac or cerebral applications. Second, the inflated balloon 222 will help to center the housing in a larger vessel to reduce the likelihood that the vessel wall will be injured by the rotor in any way. Although this may not be necessary in applications where the housing has a plurality of equiangularly spaced exhaust ports 74 because these ports will tend to make the device self-centering, as detailed above, this can be useful if such ports are not employed, as in the self-steering and self-pumping embodiments discussed below.

FIGS. 18 and 19 provide alternative fluid directing means for providing efficient recirculation of fluid in much the same manner as the balloon 222 of FIG. 17. In the embodiment of FIG. 18, the fluid directing means comprises a flexible sheath 240 which extends about a distal portion of the casing 20 and a proximal portion of the housing 70. This sheath 240 is desirably formed of a relatively flexible elastomeric material, such as a latex material such as that commonly used in the balloons of balloon catheters or the like. The sheath 240 should be adapted to be carried along the housing 70 and the casing 20; optimally, the sheath is sized so that it will fairly snugly engage the outer surfaces of these elements.

The sheath 240 should be attached to the casing 20 at a point proximal of the exhaust ports 74 and extend distally to substantially cover these ports. When the rotor (not shown) is not in operation, the sheath will lie against the ports and may substantially seal the ports. When the rotor is engaged, though, it will tend to thrust fluid out of the exhaust ports, as noted above. The force of the fluid exiting these ports will tend to inflate the sheath 240. Since the sheath is fixed adjacent its proximal end to the casing 20, the distal end of the sheath will be more inflated than the proximal end, yielding a generally frustoconical structure as shown in FIG. 18. As shown schematically by the arrows in this drawing, this will tend to direct the fluid exiting the ports back toward the distal end of the housing for another pass through the rotor.

The fluid directing means of FIG. 19 comprises a plurality of normally closed gates 250. The operation of these gates is similar to that of the sheath 240 of FIG. 18. Desirably, one gate 250 is associated with each exhaust port 74 of the housing. The gates are hingedly connected to either the housing 70 or the casing 20 at a location disposed proximally of the ports 74. The gates 250 are biased toward a closed position wherein they engage the housing to generally cover the ports 74 by any suitable means, such as with a leaf spring or the like. As with the sheath 240 of FIG. 18, when the rotor is engaged, the fluid being expelled from the housing through the ports 74 will urge the gates away from the housing and the gates will tend to redirect the fluid distally for recirculation.

If so desired, the fluid directing means could be relatively rigid and always be in he configuration used to redirect fluid distally for recirculation. However, that may lead to some problems in deployment; deployment of the device of FIG. 19 in a patient's vascular system could be hampered if the gates 250 were to remain in the position shown in the drawing. Although it is therefore preferred that the fluid directing means be selectively configurable between a relatively compact deployment configuration and an expanded configuration for redirection of fluid, it is to be understood that a permanent structure could instead be employed.

In the embodiments discussed above, the housing 70 generally includes a plurality of generally equiangularly spaced exhaust ports 74 which serve to substantially center the housing within a vessel when the rotor is rotated. As detailed above, this has some distinct advantages. FIG. 20, though, illustrates a different embodiment which utilizes only one exhaust port 74.

In the embodiment of FIGS. 20A and 20B, a single exhaust port 74 is provided in the housing 70 and this port preferably extends about no more than about 50% of the circumference of the housing, and desirably extends about substantially less than 50% of the housing's circumference. As explained above, rotation of the rotor will cause fluid to flow rearwardly, whereupon it is expelled through the single exhaust port 74. This will tend to deflect the housing toward one side of the vessel. Although this may not be as desirable as having the housing centered within the vessel, as is the housing of the embodiments described above, during maceration of thrombi, this directional urging of the distal segment of the device can be used to help deploy the device within a patient's vascular system.

When deploying a device of the earlier embodiments of the invention, a guidewire will generally be guided to a desired location within the vascular system by observing progress of the guidewire on a fluoroscope of the like and positioning the distal end of the guidewire adjacent an identified thrombus in the vascular system. The device of the invention will generally follow the guidewire, as explained above, so that it can be positioned for treatment. Generally, the rotor will not be rotated by the drive means until the housing is in the selected position for treating the patient.

By utilizing a single port 74 as shown in FIGS. 20A and 20B, though, the need for a guidewire can be eliminated. The device can be urged distally within the patient's vascular system. When the vessel branches and the operator must direct the device into one branch, for example, the rotor can be activated. This will cause the distal end of the device to be bent generally toward one wall of the vessel. By turning the device, and hence the housing 70, the direction in which the distal end of the device is bent with respect to the vascular channel can be altered as desired. Once the distal end of the housing is oriented toward the desired path, the device can once again be urged distally to move the housing into the desired branch. If so desired, the rotor can be then deactivated until it is need to orient the device toward a particular path. This process can be repeated as necessary until the desired treatment site is reached, whereupon the thrombus can be macerated by the rotor as explained in some detail above.

Utilizing a single port as shown in FIGS. 20A and 20B consequently permits an operator to steer the device within a patient's vascular system without need of a guidewire or the like. Not only can this self-steering feature potentially simplify the deployment process by eliminating the need to separately introduce and deploy a guidewire, this can also reduce the overall diameter of the device by eliminating the need for additional structure to track the guidewire, such as guidewire tracking channels 28 and 28'. This reduction in diameter can permit the device to be used in smaller vessels which may otherwise be unreachable.

FIG. 22 also illustrates an alternative housing design which permits the device to be steered during deployment by rotating the rotor. In this housing design, three or more exhaust ports 74, 75 are provided on the housing 70 for discharging fluid through the wall 72 of the housing when the rotor is rotated. These ports 74, 75 are desirably spaced generally equiangularly about the housing, as in the embodiments detailed above. Any suitable number of ports may be used; in the embodiment shown in FIGS. 22A and 22B, three ports are used, with each port being spaced from the other by about 120°.

Providing three or more generally equally sized ports spaced equiangularly about the housing will tend to produce a self-centering effect when the rotor is rotated by the drive means 100. In the embodiment of FIGS. 22, though, the two ports identified by reference number 74 are substantially the same size, but a third port 75 is substantially smaller than the main discharge ports. When the rotor is rotated, more fluid will tend to exit the two larger ports 74 than will exit the smaller port 75, which will in turn tend to deflect the housing in the direction of the side bearing the smaller port. It has been found that by making the surface area of the smaller port 75 about 20% that of either of the larger ports 74 will yield suitable steerability to the housing upon rotation of the rotor.

It should be understood that the present embodiment of the invention need not use only three ports nor have a single port smaller than the other ports in order to achieve similar self-steering properties. For example, four ports can be used, with two of the ports being smaller than the other two ports, which would induce the housing to deflect in a direction between the two smaller ports. Alternatively, one could provide a housing with a plurality of ports which are all the same size but are not spaced equiangularly about the circumference of the housing, which would also tend to deflect the housing when the rotor is driven. So long as the fluid passing through the ports which produces a deflecting force, whether by a difference in the volumes of fluid passing through the ports or by unevenly spacing the ports about the housing, this principle can be used to produce a self-steerable housing which can be advanced into position within a patient's vascular system substantially as described above in connection with FIGS. 20A and 20B.

As explained above and in the examples below, the device of the invention is quite effective at macerating clots and the like and only a rather small fraction of the clot will remain over about 100 microns in size. In certain applications, though, (e.g. use to degrade thrombi in cardiac and cerebral vessels) it may be advantageous to remove even such small volumes of oversized particles. As noted above, most prior art devices utilize aspiration to suction off fluid during operation of a thrombectomy or atherectomy device to remove unwanted clot. The generally rearward thrust of the present rotor, though, can be employed to effectively pump fluid rearwardly for disposal outside of the patient's blood without any requiring any separate aspiration equipment.

Figure 21:
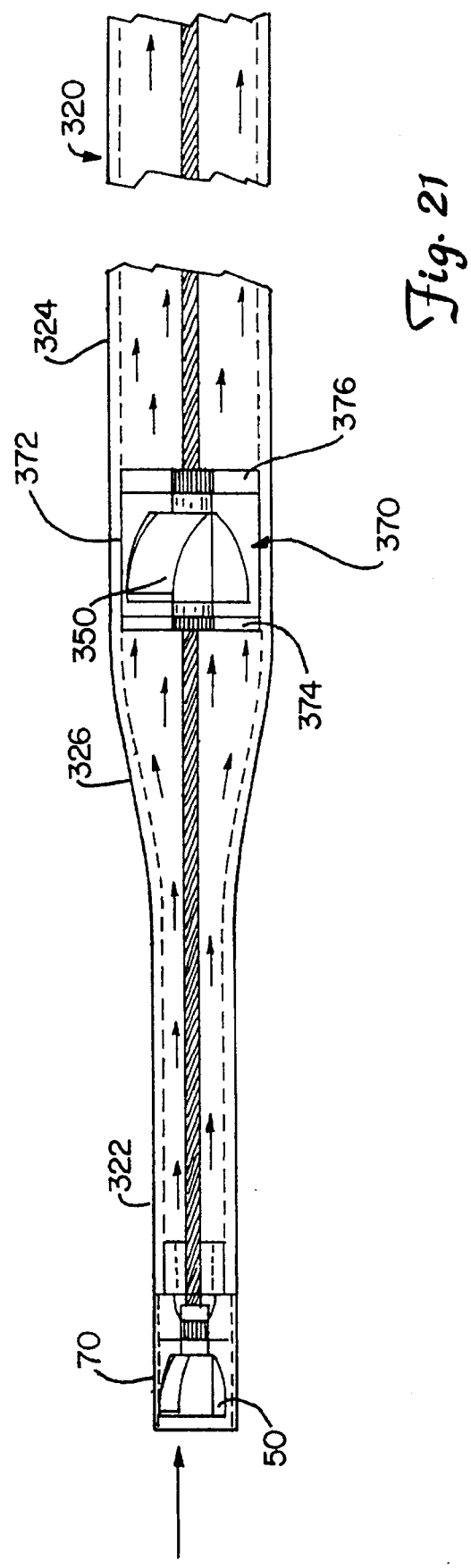
FIG. 21 is a schematic side view of a further additional embodiment which can be used to remove macerated thrombi.

In order to achieve this end, the fluid which passes through the rotor should not be permitted to exit the housing for recirculation, but should instead be retained within the housing 70 and the casing 20. FIG. 21 illustrates one particularly preferred embodiment of a self-pumping maceration device of the invention. As shown in that figure, the housing 70, which may be located at the distal end of the casing 320, does not include any exhaust ports. Instead, all of the fluid entering the distal end of the housing will be retained within the device and thrust generally rearwardly by rotation of the rotor.

As explained above, e.g. in connection with FIG. 4, the rotor of the invention is desirably a "screw type" rotor having two or more generally helical blades 56 which are oriented at an angle with respect to the main shaft of the rotor. Since the rotor is enclosed within a sealed housing, such a rotor will effectively serve as a positive displacement pump and will urge the fluid drawn into the housing rearwardly and out of the proximal end of the casing. Although the volume of the displacement of the rotor for each turn is relatively small, when the rotor is operated at relatively high speeds (such as the 100,000–135,000 rpm which is deemed to be optimal), the net volume of fluid being displaced may be sufficient to ensure that the macerated thrombi are pumped proximally out of the patient's system.

In some circumstances, though, the pressure of fluid within the casing may be too high to efficiently pump the fluid out of the patient's vascular system. In such a circumstance, it may be desirable to include a second rotor to effectively boost the rearward thrust of the first rotor to expel fluid proximally out of the casing. FIG. 21 illustrates one embodiment of such a device in accordance with the invention.

In FIG. 21, a second rotor 350 is disposed proximally of the primary maceration rotor 50. This second rotor is desirably affixed to the same shaft 10 as the forward rotor 50 so that both rotors will rotate together. The rotor 350 is carried within a sub-housing 370 having a generally cylindrical wall adapted to fit within the lumen of the casing 320 and a pair of end struts 374, 376 for providing structural support to the sub-housing. This sub-housing 370 is directly analogous to the sub-housings 280 of the multi-stage maceration embodiment shown in FIGS. 13A and 13B.

The forward rotor will tend to macerate thrombi and degrade any fibrin in the thrombi to yield a more homogenous, flowable fluid, so the second rotor 350 need not perform any great deal of maceration. Instead, the primary purpose of the second rotor 350 is to serve as a booster to assist in the pumping of the fluid. Although only a single booster rotor 350 is shown in FIG. 21, it is to be understood that any number of rotors can be spaced along the length of the casing to achieve the necessary flow of fluid therethrough.

Although both of the rotors may be of about the same size, the proximal booster rotor 350 of FIG. 21 is substantially larger than the forward rotor 50. This permits the booster rotor to displace even more fluid at the same rotational speed, thereby enhancing the pumping action of the device. This booster rotor 350 is desirably spaced a considerable distance proximally of the forward rotor 50. This will permit the forward housing 70 to be guided into relatively small vessels, e.g. for treatment of thrombi in cardiac and cerebral vessels, while the booster rotor can remain in a larger vessel.

In order to accommodate the larger second housing 370 yet fit snugly against the forward housing 70, the casing 320 of this invention optimally has a smaller diameter at its distal end adjacent the first housing 70 and a relatively large diameter along a proximal length 324. In the particularly preferred embodiment shown in FIG. 21, the casing has an elongate distal segment 322 having a first diameter, an elongate proximal segment 324 having a second, larger diameter and a tapered segment 326 disposed between the distal 322 and proximal 324 segments. This tapered portion eliminates any sharp discontinuities in the flexibility and other mechanical properties of the casing 320 to minimize any problems in deployment.

The relative lengths of the distal, proximal and tapered segments may be varied as desired for specific applications. In one preferred embodiment, the distal segment is about 10 cm to about 30 cm in length with an outer diameter of about 5.0 French and the tapered segment tapers relatively gradually from this 5.0 French distal segment to a 8.0 French proximal segment over a length of about 10 cm to about 25 cm. The proximal segment can be of any desired length which permits the distal end of the housing to be positioned at the desired treatment location within a patient's vascular system; a length of between about 50 cm and about 80 cm should work well.

The present invention also includes a drive means 100 for rotating the shaft 10 within the shaft casing 20 to cause the rotor 50 to rotate. Any suitable drive means may be used, but it is preferred that the drive means be capable of rapidly rotating the shaft and the rotor. As noted above, a rotor of the invention is desirably rotated at speeds between about 80,000 and about 150,000 rpm, with an operating range of between about 100,000–135,000 rpm being preferred.

Although the drive means may be of any type which will rotate the shaft 10 and rotor 50 at the desired speed, such as a high-speed electric motor, in a preferred embodiment an air-driven turbine is employed. As shown in FIGS. 1 and 7, this drive means includes a housing 102 having first and second sections (104 and 106, respectively). The first and second sections 104, 106 are adapted to be sealingly affixed to one another to define a short, substantially air-tight cylinder. The first section 104 desirably comprises a substantially flat, circular disc.

In the embodiment of FIG. 1, the second section 106 comprises a generally flat, circular distal face 110 and a peripheral wall 108 extends generally perpendicularly laterally from this face 110. The diameter of the first section 104 of the housing is greater than the inner diameter of the peripheral wall 108 and may be substantially equal to the outer diameter of that wall. Although the housing may be formed of any suitable material, in the preferred embodiment it is formed of a polymeric material, such as a high density, machinable plastic, which may be sonically welded to permit the first and second sections 104, 106 to be sealingly affixed to one another with ease.

As depicted in FIG. 1, an air inlet 120 and an air outlet 134 may be provided in and extend radially outwardly through the peripheral wall 108. The air inlet includes an inlet tube 124 which extends through the inlet port 122 in the housing and is adapted for attachment to an air supply. In most operating theaters, a pressurized air supply is provided, with pressures usually in the range of about 35 to about 50 psi. The inlet tube is preferably configured to be sealingly received within and retained at one end of a length of flexible hosing (not shown), the other end of which may be operatively attached to the pressurized air supply to direct pressurized air to the drive means 100 through the inlet tube 124.

As noted above, the drive means 100 desirably also includes an air outlet 134. This air outlet allows air to escape the housing 102 so that a continuous flow of air may flow into the housing through the air inlet 120. The air outlet 134 may be positioned substantially anywhere on the housing. In the embodiment shown in FIG. 1, though, the air outlet comprises a port which extends radially outwardly through the peripheral wall 108. In a particularly preferred embodiment, the air outlet 134 is positioned about the circumference of the peripheral wall relatively close to the air inlet in a direction opposite the direction of flow of air within the housing (generally clockwise in FIG. 1). In this manner, air entering the housing through the inlet 120 is forced to travel around most of the circumference of the housing before it may exit through the air outlet, serving to more rapidly accelerate the turbine to full rotational speed. In one preferred embodiment, the air outlet is provided with an outlet tube 138 carried externally of the housing to direct the flow of air exiting the housing.

An alternative embodiment of a drive means 100 which has been found to work particularly well with the present invention is shown in FIG. 7. The construction of this drive means is similar to that described above for the embodiment of FIG. 1. In particular, the housing 102 has a generally flat, circular first section 104 which is sealingly affixed to the second section 106 to define a short, substantially air-tight cylindrical housing. Once again, this housing is desirably formed of a machinable polymeric material which may be sonically welded to sealingly affix the first and second sections 104, 106 to one another.

The positions of the air inlet 120 and air outlet 134 in this embodiment differ from those in the embodiment shown in FIG. 1, though. In the present embodiment, both the air inlet and the air outlet pass through the first section 104 of the housing, i.e., at the housing's proximal end. The air inlet 120 includes an inlet port 122 which passes through the first section 104 of the housing and within which is retained an inlet tube 124. An air supply connector 126 may be provided for sealingly receiving an air supply, such as a length of flexible housing 123, in fluid communication with the inlet tube 124. At its distal end, the inlet tube 124 includes a terminal segment 130 which is positioned immediately adjacent the turbine 150, as explained in more detail below. A venturi segment 128 is provided in the inlet tube between the proximal end of the inlet tube and the terminal segment 130. The venturi segment has a larger diameter at its proximal end than at its distal end where it is sealingly affixed to the terminal segment. As is well known in the art, this relatively rapid drop in cross sectional area along the venturi segment will tend to accelerate the flow of fluid, i.e., air, as it passes from the air supply to the terminal segment 130 of the inlet tube. The axis of the inlet tube 124 is desirably substantially aligned with the axis of the generally cylindrical housing 102 so that the terminal segment 130 of the inlet tube may be positioned centrally within the housing immediately adjacent the axis of the turbine 150, as explained below.

As noted above, the air outlet 134 of the present embodiment desirably passes through the first section 104 of the housing 102. In this manner, air may be vented rearwardly out of the housing. In the preferred embodiment shown, the air outlet 134 includes an outlet port 136 which extends through the first section 104 of the housing. In a particularly preferred embodiment, a plurality of such outlet ports are utilized, the outlet ports being spaced equiangularly about the axis of the cylindrical housing with the axes (not shown) of the outlet ports 136 being generally parallel to and spaced radially outwardly from the axis of the housing. If so desired, a baffle means 140 may be provided in each outlet port 136 to diffuse the flow of air out of the housing. In one preferred embodiment, the baffle means 140 comprises a generally porous, sponge-like material which dampens the flow of air, yet permits air to pass therethrough.

The drive means 100 also includes a turbine 150 which may be caused to rotate by the flow of air through the inlet tube 124 of the air inlet. Any of a wide variety of suitable turbines may be utilized, but a preferred embodiment of a turbine for use with the present invention is shown in FIGS. 7 and 9. This turbine 150 may be formed as two separate elements, i.e., a distal segment 152 and a proximal segment 154, which are joined together to produce the turbine after being independently formed. As best seen in FIG. 9, the distal segment 152 of the turbine is generally disk-shaped and includes a plurality of generally triangular, wedge-sharped upright projections 156 spaced about its periphery. Opposing walls of adjacent projections are desirably spaced apart from and generally parallel to one another to define an uprightly open channel 158 therebetween. The wedges and resulting channels are desirably spaced equiangularly about the periphery of the distal segment 152.

The upright projections 156 desirably do not extend all the way to the center of the disk-shaped distal segment, but rather extend inwardly from the periphery a specified distance, which may be on the order of one-half the radius of the distal segment 152. This defines a generally circular central portion 160 which is bounded about its periphery by the inner edges of the upright projections 156. The channels 158 are desirably oriented generally tangentially with respect to the periphery of this central portion 160 so that as air strikes the center of the turbine, as explained in more detail below, it will be urged tangentially outwardly through the channels 158 and cause the turbine to spin. As also explained more fully below, the central portion 160 of the distal segment of the turbine is generally conical in shape and comes to a peak 162 generally along the axis of the disk-shaped distal segment. In a particularly preferred embodiment, the central portion 160 has a generally elliptical profile (as best seen in the cross sectional view of FIG. 7) rather than having a substantially flat incline.

The proximal portion 154 of the turbine is also generally disk-shaped and desirably has an outer diameter substantially equal to that of the distal segment 152. The proximal segment generally includes a central portion 170 and a peripheral portion 169 extending radially outwardly of the central portion. The peripheral portion 169 includes a plurality of fingers 168 which extend generally tangentially outwardly of the central portion 170. These fingers are adapted to be matingly received within, and fill a portion of, the channels 158 in the distal segment 152. In a preferred embodiment, the fingers 168 are generally rectangular in cross section and extend generally downwardly in FIG. 9 to define between adjacent fingers a generally triangular, wedge-shaped recess for matingly receiving the upward projections 156 of the distal segment. Although the depth of the fingers may be varied as desired, they desirably extend downwardly within the channels 158 to a depth of approximately one-half the depth of the channel.

The distal and proximal segments 152, 154 are desirably formed of an injection moldable polymeric material which may be sonically welded. This permits the individual segments to be accurately and inexpensively produced by injection molding and permits the segments to be permanently affixed to one another by the process of sonic welding. If so desired, a plurality of sacrificial nibs 166 may be spaced about the proximal and/or distal segments. During the sonic welding process, these sacrificial nibs will be broken down and will serve as a weldment for securely attaching the proximal and distal segments to one another.

The central portion 170 of the proximal segment 154 desirably includes a centrally located, generally frustoconical cap 174. When the turbine 150 is assembled, the cap will be spaced away from the central portion 160 of the distal segment to define an air flow chamber (175 in FIG. 7) therebetween. The cap includes a central port 176 through which a stream of air may pass and an upstanding lip 177 may be provided about this port. The thickness of the lip 177 may decrease proximally, as shown in FIG. 7.

As best seen in FIG. 7, when the drive means 100 is assembled, the axis of the turbine 150 substantially coincides with that of the housing 102 of the drive means and inlet tube 124 of the air inlet. The turbine is positioned immediately distally of the inlet tube. The upstanding lip 177 of the proximal segment 154 of the turbine is desirably positioned immediately adjacent the distal end of the terminal segment 130 of the inlet tube; if so desired, a short length of the lip 177 may even be rotatably positioned within the distal end of the terminal segment. This ensures that air flowing into the drive means through the inlet tube 124 will flow directly into the chamber 175 of the turbine. The air within this chamber is forced out of the turbine through the tangentially oriented channels 158 of the distal segment, causing the turbine to spin about its axis. The air then flows into the rest of the housing 102 and exits rearwardly through the air outlet 134, as described above.

As noted above, the venturi segment 128 of the inlet tube serves to accelerate the flow of air through the tube. The air thus enters the chamber 175 at a rather high flow rate, which serves to relatively rapidly accelerate the turbine to its full rotational velocity. Furthermore, by forming the turbine of relatively light weight polymeric materials, the moment of inertia of the turbine will be reduced and the turbine may be accelerated even more rapidly.

In the embodiment shown in FIG. 7, the shaft 10 of the device is connected to the turbine 150 for rotation therewith by means of a drive coupling 180. The drive coupling may be attached to the turbine and the shaft by any suitable means. In the embodiment shown, the turbine includes a generally cylindrical drive coupling recess for receiving the tubular drive coupling 180 and the drive coupling may be fixed within this recess. The drive coupling 180 desirably also includes a central recess (not separately shown) within which the shaft 10 may be received and within which the shaft may be affixed.

The drive means 100 desirably includes a distally extending, manually graspable sleeve 36, which may be formed integrally with the second section 106 of the housing. If so desired, the outer surface of this sleeve may be provided with a rougher texture (as shown in FIG. 1) to permit the sleeve to be more readily and more securely grasped by an operator of the device. The sleeve 36 is desirably tubular in shape and is adapted to receive the drive coupling 180 and a proximal portion of the shaft 10 therewithin. In order to ensure that the axes of the drive coupling 180 and turbine 150 substantially coincide with that of the sleeve 36, bearings 184 may be utilized. In the embodiment shown, two sets of bearings are used, with one being carried adjacent the distal end of the drive coupling and the other being spaced proximally at a location adjacent the drive coupling recess 182 of the turbine. Any suitable bearing may be used, but the bearing should permit the drive coupling 180 to freely rotate with respect to the sleeve 36 as the turbine and shaft are rotated.

In the embodiment shown, the sleeve 36 is elongate in shape and serves to encase structural elements of the device in addition to the drive coupling 180 and bearings 184. In the embodiment shown, a spacer 188 is carried within the sleeve at a position immediately distally adjacent the drive coupling 180. The spacer is generally tubular in shape and is adapted to be closely received within the sleeve 36. The spacer includes a central bore 190 extending through its length, the bore being sized to rotatably receive both the shaft 10 and the inner bearing 26 previously described and support these elements generally centrally along the axis of the sleeve. As noted above, the bearing 26 is not affixed to any other element of the device, including the spacer 188, but rather is "free-floating." The spacer 188 may be affixed within the lumen of the sleeve 36.

In order to ensure a substantially fluid-tight seal, an O-ring 192 or the like may be positioned between the spacer and the inner wall of the sleeve. This prevents the fluid used to drive the turbine, i.e., air, from entering the shaft casing 20 and flowing into the bloodstream. Also, it prevents fluids within the casing, such as blood or fluids which are delivered to the casing 20 through infusion line 30', from entering the housing 102 of the drive means. A portion of the spacer immediately adjacent the attachment of the infusion line 30' to the sleeve 36 is desirably spaced away from the inner wall of the sleeve in order to permit fluid to pass from the infusion line into the casing as previously explained.

Although the outer sleeve 22 of the shaft casing may be affixed directly to the sleeve 36, in a preferred embodiment the outer sleeve is affixed to a swivel connector 194 retained by the sleeve. The swivel connector includes a body 196 which is retained within the lumen of the sleeve and a distal extension 195 which protrudes distally out of the sleeve through the sleeve's distal exit 38. In order to restrict the flow of fluid from the infusion line 30' so that it will only pass into the shaft casing 20, an O-ring 196 may be disposed between the body 196 of the swivel connector and the sleeve 36. The swivel connector is desirably rotatable within the lumen of the sleeve, and a bushing 198 or the like may be utilized to ensure that the swivel connector can rotate freely with respect to the sleeve. The tubular distal extension 195 may extend forwardly of the sleeve, as noted above, and desirably is adapted to closely receive the outer sleeve 22 of the shaft casing therein. If so desired, the outer sleeve may extend along substantially the entire length of the swivel connector. The outer sleeve 22 may be sealingly affixed to the swivel connector by any suitable means which will afford a generally fluid-tight seal between the swivel connector and the shaft casing 20.

By providing a drive means 100 such as that described above, a readily available pressurized air supply may be utilized to rotate the shaft 10 and rotor 50 of the device. As noted above, the design of the preferred embodiment is configured to maximize the acceleration of the shaft. It was also noted above that if the shaft is accelerated too slowly, there is a risk that fibrin contained within a thrombus may become wrapped about the rotor rather than being broken into a number of pieces thereby. By providing a turbine which will rapidly accelerate the shaft from an initial stationary state to its full rotational speed, this risk is minimized and substantially all of the fibrin contained within a thrombus may be degraded into very small, discrete pieces.

A number of experiments have been carried out utilizing the invention described above. First, bench tests were performed in vitro by first artificially producing thrombi and then breaking down the thrombi with the present invention. Human blood clots were produced by mixing packed red blood cells and whole plasma with calcium chloride and allowing the blood to clot and consolidate for a period of 7–10 days. This produces a clot with a moderate degree of fibrin content but not a great deal of calcification. The clots so formed ranged in length from about 3 to about 10 cm and were between 1 cm and about 3 cm in diameter. These artificially produced clots were then placed in test tubes and the distal end of a device according to the invention was placed within a test tube. Air was supplied to the drive means 100 to turn the rotor at between about 100,000 and about 135,000 rpm. The homogenized material was then filtered through a series of nylon screens having varying pore sizes. The first screen had a 200 micron pore size, the second was 100 microns, the third was 47 microns, and the final screen had 13 micron pores.

It was found that by driving the rotor when it is positioned at or adjacent the site of the clot for a period of between 15 and 45 seconds, clots could be substantially completely degraded into rather fine particles. The larger clots would generally require longer periods of time, such as 45 seconds, in order to be completely degraded, while smaller clots may be degraded in 15 seconds or less. As a result of this testing, it was found that the invention may readily degrade thrombi in less than a minute to a point wherein 99.76% by weight of the thrombus will pass through a 13 micron screen. Of the remaining ¼ of 1%, approximately 0.10% of the particles exceeded 200 microns, 0.03% were between 200 and 100 microns in size, 0.05% were between 100 and 47 microns, and 0.8% of the particles, by weight, were between 47 and 13 microns in size. As it is generally accepted that particle sizes less than about 90–100 microns do not pose any significant risk of forming additional thrombi if left within the bloodstream, these results indicate that the invention can degrade upwards of 99.8% of a thrombus to essentially harmlessly sized particles in less than a minute.

Animal testing has also been conducted. Artificial blood clots were formed in mongrel dogs in a manner similar to that noted above. By known techniques, the invention was guided to a position wherein the rotor was adjacent the suspected location of such a clot and the rotor was actuated by supplying air to the drive means 100. The dogs were then sacrificed and a series of tests were performed to determine the level of hemolysis (rupturing of the red blood cells) and to ensure that no damage was done to the intima of the vessels. In none of these tests was any clinically significant degree of hemolysis or trauma to the vessel walls noted. Over 90% of the animals tested averaged 97% dissolution of the artificially created occlusive clot. As a "successful" dissolution is generally defined as improving vessel patency, i.e., widening the opening in the vessel, by 50%, these results indicate that the device is highly successful in degrading thrombi within the vessels of a living mammal without any appreciable degree of harm to the blood cells or to the vessel walls.

While a preferred embodiment of the present invention has been described, it should be understood that various changes, adaptations and modifications may be made therein without departing from the spirit of the invention and the scope of the appended claims.

We claim:

1. A mechanical thrombus maceration device comprising:
   a. an elongate, flexible shaft having proximal and distal ends, the shaft being adapted to be guided along a vascular path and being rotatable within a vascular channel having a vascular wall;
   b. a plurality of rotors affixed to the shaft for rotation therewith, the rotors being spaced apart from one another along the shaft;
   c. drive means for rapidly rotating the shaft; and
   d. a rotor housing enclosing at least one of the rotors and within which said rotor rotates, the housing comprising a generally cylindrical wall substantially surrounding said rotor.

2. The invention of claim 1 wherein said rotors are carried along a distal segment of the shaft and the rotor housing encloses all of the rotors and includes a first discharge port passing through the wall of the housing at a location proximal of the distal-most rotor and an intake port disposed distally of the proximal-most rotor.

3. The invention of claim 1 further comprising a casing about the shaft, wherein a first of the rotors is positioned adjacent a distal end of the device and is adapted to macerate thrombi entrained in fluid in a patient's vascular system and to displace a fluid proximally, and a second of the rotors is disposed proximally of the first rotor and is adapted to displace a fluid proximally, the first and second rotors acting together to draw fluid into the device adjacent its distal end and pump at least a portion of that fluid rearwardly through the casing for removal from the patient's vascular system.

4. The invention of claim 3 wherein the second rotor is larger than the first rotor and displaces a greater volume of fluid than the first rotor when the shaft is rotated.

5. The invention of claim 4 wherein the casing is generally tubular and has a distal segment, a proximal segment and a tapered segment disposed between the distal and proximal segments, the proximal segment having a larger diameter than the distal segment, the tapered segment tapering relatively gradually from a diameter adjacent its proximal end substantially equal to the diameter of the proximal segment to a diameter adjacent its distal end substantially equal to the diameter of the distal segment.

6. A mechanical thrombus maceration device comprising:
   a. an elongate, flexible shaft having proximal and distal ends, the shaft being adapted to be guided along a vascular path and being rotatable within a vascular channel having a vascular wall;
   b. a rotor affixed to the shaft adjacent the distal end thereof for rotation therewith;
   c. drive means for rapidly rotating the shaft;
   d. a rotor housing carried about the rotor and within which the rotor rotates, the housing comprising a generally cylindrical wall substantially surrounding the rotor and having at least one discharge port formed therein for discharging fluid out of the housing when the rotor is rotated, the port being spaced proximally of the rotor; and
   e. fluid directing means associated with the discharge port for directing fluid from the discharge port back toward the rotor.

7. The invention of claim 6 wherein the fluid directing means is expandable from a collapsed state for deployment to an expanded position wherein it directs fluid from the discharge port back toward the rotor.

8. The invention of claim 7 wherein the fluid directing means comprises a selectively inflatable balloon positioned adjacent a distal end of the housing.

9. The invention of claim 8 wherein the balloon is sized to engage the wall of the vessel and substantially fill the vessel's lumen.

10. The invention of claim 7 wherein the fluid directing means comprises a sheath formed of a flexible elastomeric material attached to the device proximally of the port, the sheath in its collapsed state covering at least a portion of the port and being expanded into its expanded state by fluid discharged through the port.

11. The invention of claim 10 wherein the sheath in its expanded state is generally frustoconical in shape, having a proximal end narrower than a distal end.

12. The invention of claim 6 wherein the fluid directing means comprises a gate carried adjacent the port, the gate being oriented at an angle with respect to the housing when fluid is discharged from the housing through the port to direct discharged fluid distally of the port.

13. The invention of claim 12 wherein the gate is normally biased toward the housing to substantially cover the port, the gate being hingedly attached to the device such that it will pivot outwardly of the housing in response to fluid being discharged from the port.

14. The invention of claim 13 wherein the housing includes a plurality of ports, one gate being positioned adjacent each port.

15. A mechanical thrombus maceration device comprising:
   a. an elongate, flexible shaft having proximal and distal ends, the shaft being adapted to be guided along a vascular path and being rotatable within a vascular channel having a vascular wall;
   b. a rotor affixed to the shaft adjacent the distal end thereof for rotation therewith;
   c. drive means for rapidly rotating the shaft; and
   d. a rotor housing carried about the rotor and within which the rotor rotates, the housing comprising a generally cylindrical wall substantially surrounding the rotor and having at least one port formed therein, the surface area of the port or ports being distributed unevenly about the circumference of the housing such that when a fluid is ejected through the ports within a vascular channel, the housing will tend to deflect toward one side of the vascular channel to permit the device to be steered during deployment thereof within a patient's vascular system.

16. The invention of claim 15 wherein the housing has only one port formed therein.

17. The invention of claim 15 wherein the housing has first and second ports formed therein, the first port having a greater surface area than the second port.

18. The invention of claim 17 wherein the housing has at least three of said ports formed therein, the ports being substantially equiangularly spaced about the circumference of the housing.

* * * * *